US012586686B1

(12) United States Patent  
Gollub

(10) Patent No.: US 12,586,686 B1  
(45) Date of Patent: Mar. 24, 2026

(54) TREATMENT RECOMMENDATIONS USING GENOMIC DATA AND REINFORCEMENT LEARNING

(71) Applicant: PointHealth AI, INC., San Francisco, CA (US)

(72) Inventor: Rachel Mara Gollub, San Jose, CA (US)

(73) Assignee: PointHealth AI, Inc., San Francisco, CA (US)

( * ) Notice: Subject to any disclaimer, the term of this patent is extended or adjusted under 35 U.S.C. 154(b) by 1 day.

(21) Appl. No.: 19/050,932

(22) Filed: Feb. 11, 2025

(51) Int. Cl.
| | |
|---|---|
| *G16H 50/20* | (2018.01) |
| *G06N 3/092* | (2023.01) |
| *G16H 10/60* | (2018.01) |
| *G16H 20/10* | (2018.01) |

(52) U.S. Cl.
CPC ............. *G16H 50/20* (2018.01); *G06N 3/092* (2023.01); *G16H 10/60* (2018.01); *G16H 20/10* (2018.01)

(58) Field of Classification Search
CPC ............................... G16H 50/20; G16H 10/60
See application file for complete search history.

(56) References Cited

U.S. PATENT DOCUMENTS

| | | | | |
|---|---|---|---|---|
| 11,889,819 | B2 * | 2/2024 | Worth ................... | G06F 18/217 |
| 2017/0116379 | A1 * | 4/2017 | Scott ...................... | G16H 50/20 |
| 2022/0093217 | A1 * | 3/2022 | Abraham ............... | G16B 40/20 |
| 2022/0319658 | A1 * | 10/2022 | Abraham ............... | G16H 20/10 |
| 2023/0368915 | A1 * | 11/2023 | Abraham ............. | G01N 33/574 |
| 2024/0076744 | A1 * | 3/2024 | Blidner ................. | G16B 25/10 |

* cited by examiner

*Primary Examiner* — Jay M. Patel  
(74) *Attorney, Agent, or Firm* — Landfall IP

(57) ABSTRACT

Methods, systems, apparatuses, devices, and computer program products are described. A system may use a rules engine and a reinforcement learning artificial intelligence (AI) model to recommend treatment options for a patient. In some examples, the AI model may be trained for a specific diagnosis. The system may receive patient information including the patient's diagnosis, genomic profile (e.g., partial or full genomic information), and treatment history. The system may input the genomic profile into the rules engine to determine any relevant treatment modifications for the user based on biomarkers in the genomic profile. The system may additionally input the patient information into the AI model to determine a set of treatment option recommendations and corresponding confidence metrics. The system may send the treatment option recommendations (e.g., which in some cases may be modified based on the output of the rules engine) to a user device for display.

20 Claims, 10 Drawing Sheets

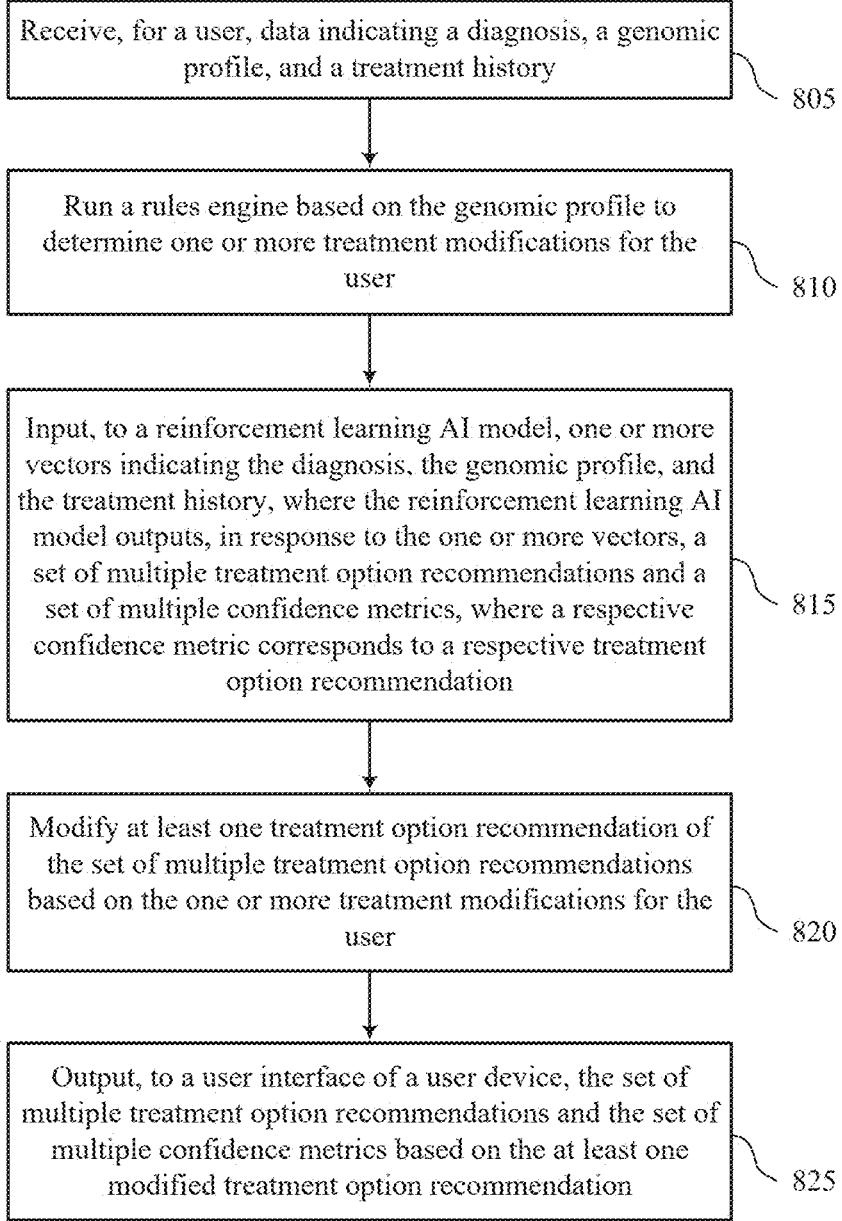

Receive, for a user, data indicating a diagnosis, a genomic profile, and a treatment history

805

Run a rules engine based on the genomic profile to determine one or more treatment modifications for the user

810

Input, to a reinforcement learning AI model, one or more vectors indicating the diagnosis, the genomic profile, and the treatment history, where the reinforcement learning AI model outputs, in response to the one or more vectors, a set of multiple treatment option recommendations and a set of multiple confidence metrics, where a respective confidence metric corresponds to a respective treatment option recommendation

815

Modify at least one treatment option recommendation of the set of multiple treatment option recommendations based on the one or more treatment modifications for the user

820

Output, to a user interface of a user device, the set of multiple treatment option recommendations and the set of multiple confidence metrics based on the at least one modified treatment option recommendation

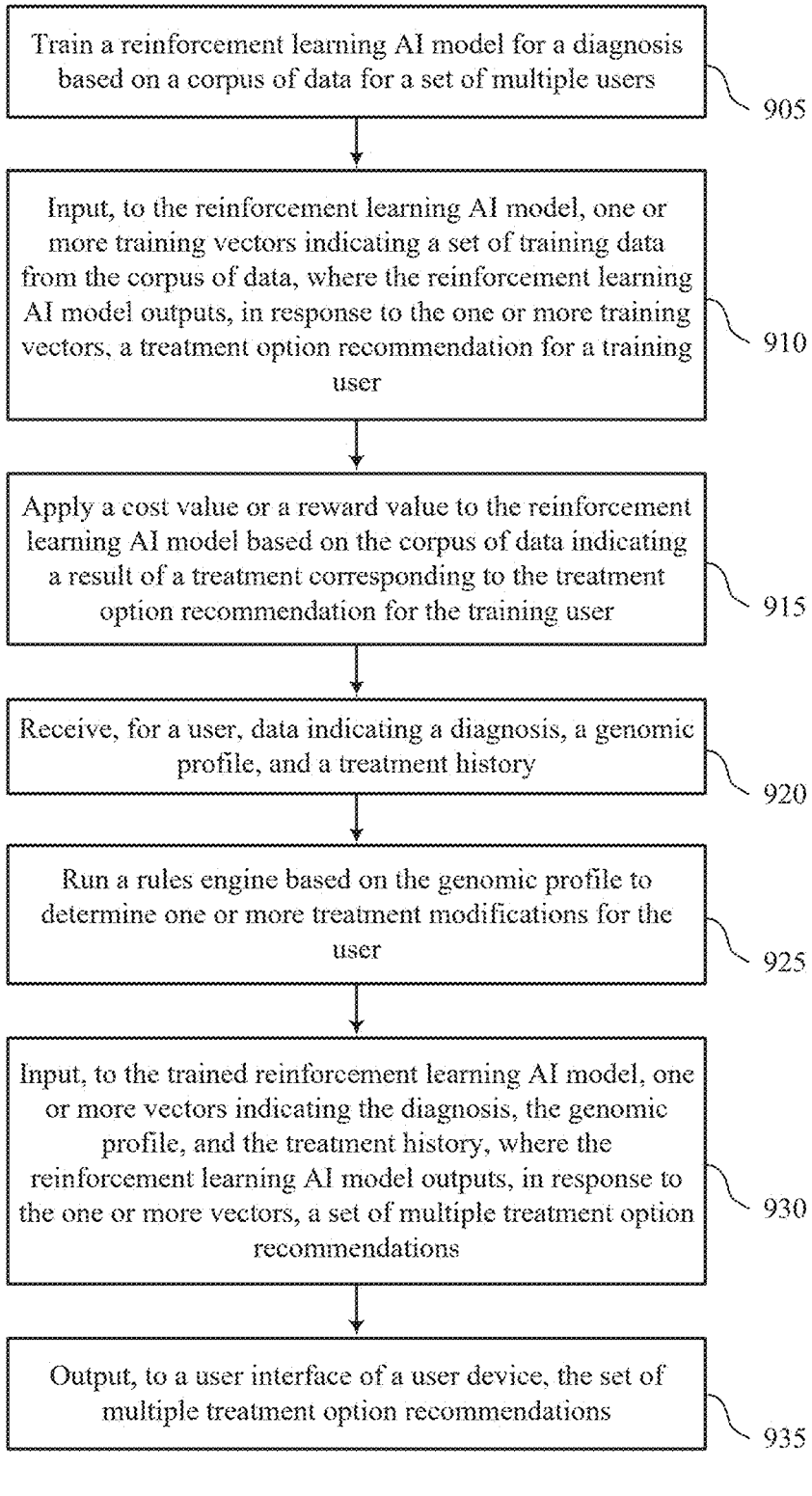

Train a reinforcement learning AI model for a diagnosis based on a corpus of data for a set of multiple users

905

Input, to the reinforcement learning AI model, one or more training vectors indicating a set of training data from the corpus of data, where the reinforcement learning AI model outputs, in response to the one or more training vectors, a treatment option recommendation for a training user

910

Apply a cost value or a reward value to the reinforcement learning AI model based on the corpus of data indicating a result of a treatment corresponding to the treatment option recommendation for the training user

915

Receive, for a user, data indicating a diagnosis, a genomic profile, and a treatment history

920

Run a rules engine based on the genomic profile to determine one or more treatment modifications for the user

925

Input, to the trained reinforcement learning AI model, one or more vectors indicating the diagnosis, the genomic profile, and the treatment history, where the reinforcement learning AI model outputs, in response to the one or more vectors, a set of multiple treatment option recommendations

930

Output, to a user interface of a user device, the set of multiple treatment option recommendations

TREATMENT RECOMMENDATIONS USING GENOMIC DATA AND REINFORCEMENT LEARNING

FIELD OF TECHNOLOGY

The present disclosure relates generally to data processing and secure data storage, and more specifically to treatment recommendations using genomic data and reinforcement learning.

BACKGROUND

In medicine, a patient's genomic data may include a set of biomarkers that indicate how the patient is likely to respond to specific drugs. Such genomic data for a patient may improve a doctor's ability to effectively treat the patient, for example, by modifying treatment option recommendations based on one or more of these biomarkers. However, many patients may have incomplete genomic data, such as a partial genetic sequencing or a subset of identified biomarkers. A doctor may fail to effectively recommend a treatment for a patient with incomplete genomic data. Additionally, or alternatively, the known correlations between biomarkers and drug responses may fail to capture other trends in how patients' genetic profiles predict treatment efficacy. Furthermore, a patient's genomic data may include sensitive medical information. Surfacing this data to entities, such as insurance companies, may potentially compromise the patient's privacy and negatively affect the patient's healthcare coverage.

BRIEF DESCRIPTION OF THE DRAWINGS

FIGS. 8 through 10 show flowcharts illustrating methods that support treatment recommendations using genomic data and reinforcement learning in accordance with aspects of the present disclosure.

DETAILED DESCRIPTION

Figure 1:
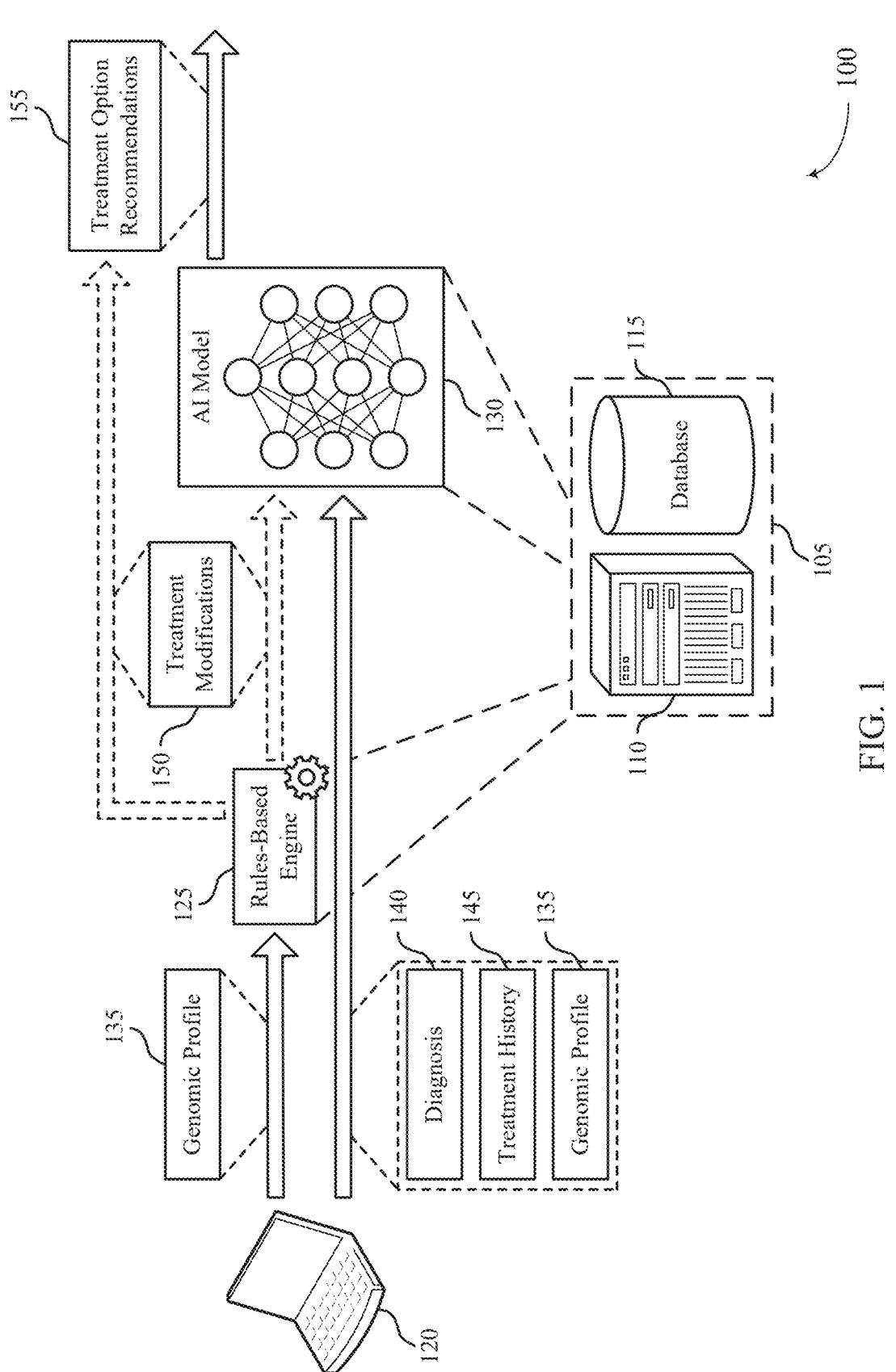
FIG. 1 illustrates an example of a system that supports treatment recommendations using genomic data and reinforcement learning in accordance with aspects of the present disclosure.

Collection and management of genomic data may provide a variety of benefits for different entities within the healthcare industry. For example, research groups may use genomic data from multiple people to support robust genomic analysis. Additionally, or alternatively, determining a genomic profile for a patient may provide insights on how the patient will react (or is expected to react) to specific drugs or other treatments. A doctor, or other medical professional, may use such insights to improve medical care for the patient. For example, the doctor may prescribe a treatment based on the patient's genomic profile. A genomic profile may include any quantity of genetic information for a patient, such as a full genetic sequencing, a partial genetic sequencing, a list of biomarkers, or any combination thereof. A biomarker may be any measurable characteristic of a gene that indicates a person's response (or likely response) to a drug or other treatment. Using genomics to support a doctor's prescribed treatment may also improve an authorization process from an insurer. For example, the genomics may indicate that the doctor's recommended treatment is the treatment option most likely to improve the patient's health. However, many patients may have incomplete genomic data, limiting a doctor's ability to determine a best treatment. Additionally, some correlations between genomic data and treatment efficacy may be unknown or unverified, further limiting the doctor's ability to determine the best treatment. In some examples, surfacing genomic data to an insurer may compromise a patient's privacy, potentially enabling the insurer to implement coverage changes for the patient based on the patient's genomic data.

A system may implement a platform or service that securely manages genomic data to provide insights to doctors and insurers (e.g., insurance companies) without compromising the security of patient data. For example, the platform or service may provide a single pathway for leveraging genomic data to improve patient care, support genomic analysis, and provide insights to insurance companies without revealing the underlying genomic data. The platform or service may use artificial intelligence (AI) techniques to improve treatment recommendations based on patient similarity. For example, a device or system may recommend treatment options for a patient using a rules engine (e.g., rules-based engine), a reinforcement learning AI model (or other AI model or machine learning (ML) technique), or both (e.g., in a two-step process).

A device or system may receive, for a user (e.g., a patient), data indicating a diagnosis for the patient, a genomic profile of the patient, and a treatment history for the patient. The treatment history may map the patient's journey up to this point in time (e.g., the treatments prescribed to the patient, the results of these treatments, the order of these treatments). In some examples, the data may additionally, or alternatively, include other health records, claims, social determinants of health, or any combination thereof for the patient. The device or system may run a rules engine based on the genomic profile to determine one or more treatment modifications for the patient. For example, the rules engine may indicate, based on one or more biomarkers in the patient's genomic profile, to remove a drug from the treatment options for the patient, modify a drug dosage for the treatment options for the patient, remove a specific combination of drugs from the treatment options for the patient, or any combination thereof. Accordingly, the rules engine may operate as a first-pass filter to ensure potentially dangerous drugs, dosages, and drug combinations are not recommended by the reinforcement learning AI model.

The device or system may input, to the reinforcement learning AI model, one or more vectors representing (or otherwise indicating) the diagnosis, the genomic profile, the treatment history, or any combination of these or other data associated with the patient. In some examples, the reinforcement learning AI model may leverage Q-learning, such as in a double deep Q network (DQN) model. The device or system (or a different device or system) may train the reinforcement learning AI model based on patient similarities (e.g., in a vector space) to output treatment recommendations. Because the reinforcement learning AI model may be trained using data sets with genetic profiles that include different quantities of information (e.g., some with full genetic sequencing, some with partial genetic sequencing, some with a set of biomarkers, some with no—or insignificant—official genetic information), the trained model may support relatively accurate treatment recommendations based on any amount of genomic data provided for a patient.

In some cases, the platform or service may host different reinforcement learning AI models for different diagnoses. For example, a first AI model may be trained to recommend treatment options for patients with a first diagnosis, while a second AI model may be trained to recommend treatment options for patients with a second diagnosis. The reinforcement learning AI model may output, in response to the input vectors, a set of treatment option recommendations and corresponding confidence metrics. For example, the output may indicate a first treatment option with a 60% likelihood of being the best treatment, a second treatment option with a 20% likelihood of being the best treatment, and a third treatment option with a 15% likelihood of being the best treatment. In some cases, the AI model may output a configured quantity of treatment option recommendations (e.g., the top n options). In some other cases, the AI model may output treatment options with a confidence metric that satisfies a threshold (e.g., a greater than 5% likelihood of being the best treatment). Because the AI model is trained based on patient similarities, the treatment option recommendations may reflect correlations between genomic data and treatment efficacies that are not known for specific biomarkers. The rules engine may fail to account for such correlations. However, the device or system may also modify the output of the reinforcement learning AI model based on the output of the rules engine. For example, the device or system may remove or modify one or more of the treatment option recommendations, recalculate one or more of the confidence metrics, or both. Additionally, or alternatively, the output of the rules engine may be used as an additional input to the reinforcement learning AI model. Accordingly, the reinforcement learning AI model may identify more accurate treatment recommendations based on patient similarity than the rules engine, while the rules engine may protect the AI model from recommending treatment options that are known to be dangerous for patients with specific genetic profiles.

In some examples, the platform or service may send the set of treatment option recommendations, the corresponding confidence metrics, or both to a user device for display. For example, the platform or service may send the top treatment option recommendation or the top n treatment option recommendations for display on a doctor's, or other healthcare provider's, computer. The doctor may prescribe a treatment for the patient based on the treatment option recommendation(s). Additionally, or alternatively, the platform or service may send similar information to an insurer. For example, if the doctor prescribes the top recommended treatment option, the platform or service may trigger sending a request for prior authorization to the insurer. The request may indicate that the doctor prescribed the treatment predicted to be the best treatment (e.g., according to the confidence metrics) based on a genomic analysis. Accordingly, the platform or service may use the genomic data to improve patient care and insurance authorization without compromising the security of the patient's genomic profile or the other genomic data used to train the reinforcement learning AI model.

Aspects of the disclosure are initially described in the context of a system supporting treatment recommendations using genomic data and AI techniques. Additional aspects of the disclosure are described with reference to a reinforcement learning process and a patient similarity analysis. Aspects of the disclosure are further illustrated by and described with reference to process flows, apparatus diagrams, system diagrams, and flowcharts that relate to treatment recommendations using genomic data and reinforcement learning.

FIG. 1 illustrates an example of a system 100 that supports treatment recommendations using genomic data and reinforcement learning in accordance with aspects of the present disclosure. The system 100 may be an example of a platform or service that provides genomic analysis for doctors, insurers, or both. The system 100 may include a processing system 105, which may include one or more processing devices 110, one or more databases 115, or a combination thereof. A processing device 110 may be an example of any processing device or system, such as an application server, a database server, a cloud-based server or service, a worker server, a server cluster, a virtual machine, a container, a network device, a user device, or any combination of these or other computing devices. A database 115 may be an example of any data storage device or system, such as a single database, a distributed database, multiple distributed databases, a data store, a data lake, an emergency backup database, memory storage at a user device, or any combination of these or other data storage devices. The processing system 105 may support one or more AI components that provide treatment option recommendations 155 for users (e.g., patients) using genomic data. For example, the processing system 105 may include a rules-based engine 125, an AI model 130 (such as a reinforcement learning AI model), or both to improve treatment recommendation.

The system 100, including the processing system 105, may support a service that provides a single pathway for users (e.g., patients, doctors, or other healthcare professionals) to receive treatment recommendations based on a genomic analysis of a patient (e.g., among other factors and historical data) and trigger approval of a treatment from an insurance provider without compromising the security of the patient's medical data. That is, the service may operate between healthcare professionals, insurance companies, and organizations performing data analytics to provide benefits for each of these entities. In some examples, the service may support one or more plans for different users. For example, the service may offer one or more patient plans. When a medical provider gains a new patient on the service's plan, the patient may undergo genetic testing to determine a genomic profile 135 (e.g., a full or partial genomic profile 135) for the patient that may be used by the service. In some examples, the new patient may perform a spit test, blood test, or both for genetic testing, and the results of the genetic testing may be sent to the system 100 for secure storage (e.g., in the database 115). The database 115 may store the genetic information for the patient in a Health Insurance Portability and Accountability Act (HIPAA)—compliant graph database with encryption at rest. The system 100 may refrain from sharing this data with any other systems or companies (e.g., using programmatic, mechanical, or electrical safeguards to ensure the data cannot be shared externally).

A doctor or other healthcare professional may use the system 100 to improve patient treatment while securely handling sensitive medical data for the patients. For example, a doctor may diagnose a patient with a specific condition. Oftentimes, such a diagnosis 140 may be treated in multiple different ways based on a multitude of factors. Rather than selecting a treatment option based on the doctor's intuition, which in many cases may involve underlying biases or outdated methods, the doctor may use the treatment recommendation service supported by the system 100 to provide one or more treatment option recommendations 155 in response to the diagnosis 140, a treatment history 145 for the patient, and a genomic profile 135 for the patient.

For example, a human's genomic profile 135 may indicate important information about how that person can be treated for specific conditions. That is, different patients may respond differently to drugs based on the patients' genetic characteristics. Thousands of biomarkers (which may alternatively be referred to simply as "markers") have been identified on genes that indicate pharmacogenomic information. For example, a first biomarker on a first gene may indicate that a patient is allergic to a first drug. A second biomarker on a second gene may indicate that a second drug is ineffective for a patient. A third biomarker on a third gene may indicate that a patient has a relatively higher or lower tolerance (e.g., based on absorption, distribution, or metabolism) of a third drug, such that a dosage of the third drug may be adjusted to effectively treat the patient. A fourth biomarker on a fourth gene may indicate that a specific combination of drugs may negatively affect a patient. Other biomarkers may indicate other pharmacogenomic information for a patient. Additionally, or alternatively, combinations of biomarkers on a same gene or across genes may indicate this information or other pharmacogenomic information.

Accordingly, obtaining at least a partial genomic profile 135 for a patient may improve treatment recommendations for the patient. For example, a genomic profile 135 may include any quantity of information relating to a user's biomarkers. In some examples, the genomic profile 135 may include genetic sequencing data (e.g., microarray data) for a patient, such as a full or partial genetic sequencing for the patient. In some other examples, the genomic profile 135 may include a subset of information based on a pharmacogenomic scan or other analysis that indicates at least a subset of biomarkers or predicted drug responses based on one or more biomarkers.

A user device 120 may send patient data for analysis by the processing system 105. Additionally, or alternatively, the user device 120 may perform the analysis. The user device 120 may send the genomic profile 135 (e.g., the available genomic information for a user), the diagnosis 140, and the treatment history 145 for a user (e.g., a patient). Alternatively, the user device 120 may send patient identification information, and the processing system 105 may retrieve one or more of the genomic profile 135, the diagnosis 140, and the treatment history 145 from a medical database (e.g., a database 115). In some examples, the user operating the user device 120 may be the patient, a doctor, or another healthcare professional. The user device 120 may be an example of a laptop, a desktop, a smartphone, a smartwatch, or any other device that supports inputs and outputs for a user operating the device.

The processing system 105 may receive the data from the user device 120 and may perform a rules-based analysis of the data (or a portion of the data). For example, the processing system 105 may include a rules-based engine 125. The processing system 105 may input the genomic profile 135 for the patient into the rules-based engine 125. Based on the genomic profile 135, the rules-based engine 125 may output an indication of treatment modifications 150. For example, the rules-based engine 125 may be trained based on known pharmacogenomic effects of biomarkers. The rules-based engine 125 may analyze the patient's biomarkers indicated by the genomic profile 135 and may identify potential allergies, metabolic issues, problematic drug combinations, or any other known drug-related information provided by the biomarkers. The rules-based engine 125 may output one or more treatment modifications 150, such as drugs to remove from potential treatment options, drug combinations to remove from potential treatment options, drug dosage recommendations for potential treatment options, or any combination thereof. In some cases, based on the biomarkers, the rules-based engine 125 may not output any treatment modifications 150. In such cases, the AI model 130 may perform the treatment recommendation independently (e.g., without input from the rules-based engine 125).

The rules-based engine 125 may provide a first pass for improving treatment option recommendations 155 based on known correlations between genetic biomarkers and drug (or other treatment) responses. However, in some cases, genetic information may support additional insights based on patient similarities that is more complex than rules-based determinations. The processing system 105 may support a second pass for improving the treatment option recommendations 155 using an AI model 130. The AI model 130 may use additional inputs (e.g., beyond the user's genomic profile 135) to determine the treatment option recommendations 155. In some examples, the AI model 130 may be trained specifically for a diagnosis 140. For example, the processing system 105 may support different AI models 130 for different conditions, such as a first AI model 130 trained specifically to provide treatment recommendations for depression, a second AI model 130 trained to provide treatment recommendations for diabetes, a third AI model 130 trained to provide treatment recommendations for Human Immunodeficiency Virus (HIV), or any combination of these and other AI models for other diagnoses.

In some examples, the processing system 105 may support a biomarker analysis (e.g., using a rules-based engine 125 or other analytics techniques), an AI model 130, or both in any order. In some cases, the processing system 105 may first use the rules-based engine 125 to determine treatment modifications 150 and may use the treatment modifications 150 as an input to the AI model 130 to determine the treatment option recommendations 155. In some other cases, the processing system 105 may first use the AI model 130 to determine treatment option recommendations 155 and may use the rules-based engine 125 to modify the treatment option recommendations 155 output by the AI model 130. In yet some other cases, the processing system 105 may operate the rules-based engine 125 and the AI model 130 in parallel. Additionally, or alternatively, the processing system 105 may support one or more biomarker analyses, one or more rules-based engines 125, one or more AI models 130, or any combination thereof according to any order (e.g., processing in sequence, in parallel, or some combination thereof) to determine the treatment option recommendations 155.

The processing system 105 may select, or otherwise determine, an AI model 130 based on the diagnosis 140 and may input, to the AI model 130, values representative of the genomic profile 135, the treatment history 145, the treatment modifications 150, or any combination of these or other patient information. In response to the inputs, the AI model 130 may output one or more treatment option recommendations 155. The AI model 130 may be trained using patient similarities, such that the AI model 130 recommends treatments that were successful for relatively similar patients (e.g., with similar genomic profiles 135, similar treatment histories 145, similar social determinants of health, similar health records, or any combination of these or other patient information). In some examples, the AI model 130 may output a single treatment option recommendation 155. In some other examples, the AI model 130 may output a set of treatment option recommendations 155 along with corresponding confidence metrics. For example, the AI model 130 may output a first treatment option recommendation 155 with a first confidence metric (e.g., 0.4, indicating a predicted 40% likelihood that the first treatment option recommendation 155 is the best treatment option for the patient), a second treatment option recommendation 155 with a second confidence metric (e.g., 0.25), a third treatment option recommendation 155 with a third confidence metric (e.g., 0.14), and a fourth treatment option recommendation 155 with a fourth confidence metric (e.g., 0.08). The AI model 130 may output any quantity of treatment option recommendations 155, for example, based on a configured quantity of treatment options to recommend, a configured threshold confidence metric, or some combination thereof. The quantity of treatment option recommendations may be automatically determined or may be configured by a user (e.g., a doctor requesting the top 5 recommendations). In some examples, the processing system 105 may update the treatment option recommendations 155 based on the treatment modifications 150.

A treatment option recommendation 155 may include a drug recommendation, a surgery recommendation, a therapy recommendation, a test recommendation, a follow-up recommendation, or any combination thereof. A recommendation may include dosage information, timing information (e.g., how long to take a drug, when to run tests, when to follow up with the doctor), or both. Because of the model training, a treatment option recommendation 155 may, in some cases, be unique. For example, the full treatment plan may not match any specific treatment plan used before for another patient (although the steps in the treatment plan may be used in other treatment plans for other patients). In some examples, the treatment option recommendation 155 may additionally indicate a percentage of patients that the recommended treatment plan worked for (e.g., improved the health of the patients). In some examples, the treatment option recommendation 155 may highlight, or otherwise emphasize, key differentiators or key steps of the recommended treatment plan.

In some cases, the processing system 105 may send the treatment option recommendations 155 to the user device 120 for display. For example, the user device 120 may display the treatment option recommendations 155, the corresponding confidence metrics, or both to a healthcare professional to support the healthcare professional selecting a treatment for the user (e.g., the patient). By providing multiple options, the system 100 may allow a doctor to select a treatment option recommendation 155 based on specific patient information not indicted by genomic biomarkers (e.g., not input into the AI model 130), new information from the Center for Disease Control (CDC), latest best practices, or any combination thereof. In some cases, the user device 120 may support user interaction with the treatment option recommendations 155. For example, the user (e.g., the doctor) may modify one or more aspects of the treatment option recommendations 155, and the AI model 130 may provide an updated confidence metric for the modified treatment. For example, the user may adjust the timing of a test, the dosage of a drug, or some other part of the treatment option recommendations 155, and the system 100 may provide an updated likelihood that the modified treatment is the best treatment. Additionally, or alternatively, the system 100 may provide a warning (e.g., if the doctor modifies a drug dose to a dangerous quantity or adds a drug that may be dangerous to the patient based on the patient's genomic profile 135).

Additionally, or alternatively, the processing system 105 may send the treatment option recommendations 155 to an insurance company to help with treatment authorization. For example, the message sent to the insurance company may indicate, based on genomic analysis, the treatment that the doctor should recommend (e.g., the treatment with the greatest confidence metric).

The system 100 or a similar system may be implemented to provide one or more of the following potential benefits. By using an AI model 130 trained according to patient similarities, the AI model 130 may mitigate co-morbidities contaminating the patient data. For example, patients with one disease may be likely to have a second disease that affects treatment results. However, by using patient similarities, the AI model 130 may be trained to account for the likelihood of such co-morbidities. Additionally, or alternatively, the system 100 may mitigate the negative effects of doctor biases. For example, by using biomarkers as a key value in treatment recommendations, the AI model 130 may deemphasize factors such as race and gender, reducing common biases in medical fields. For example, the AI model may recommend drug dosages based on genomic information, rather than based on race or gender.

Additionally, or alternatively, by storing the patient genomic profiles 135 in a secure database 115 (e.g., a graph database, a document database) with encryption at rest, the system 100 may ensure the genomic data is used to accurately train the AI model 130 without compromising the security of the genomic data. For example, when a returning patient provides updated information to the system 100 (e.g., updated genomic data, an update to the patient's journey such as a new treatment or results of the new treatment), the system 100 may create a new node in the graph database for the patient, rather than updating an existing node. Because the graph database refrains from storing personal identifiable information (PII) for the patients, the system 100 may not be able to identify nodes in the graph database corresponding to the same patient. Such a system for creating nodes may ensure privacy is upheld for the patients and their medical information is stored securely.

It should be appreciated by a person skilled in the art that one or more aspects of the disclosure may be implemented in a system 100 to additionally, or alternatively, solve other problems than those described above. Furthermore, aspects of the disclosure may provide technical improvements to "conventional" systems or processes as described herein. However, the description and appended drawings only include example technical improvements resulting from implementing aspects of the disclosure and accordingly do not represent all of the technical improvements provided within the scope of the claims.

Figure 2:
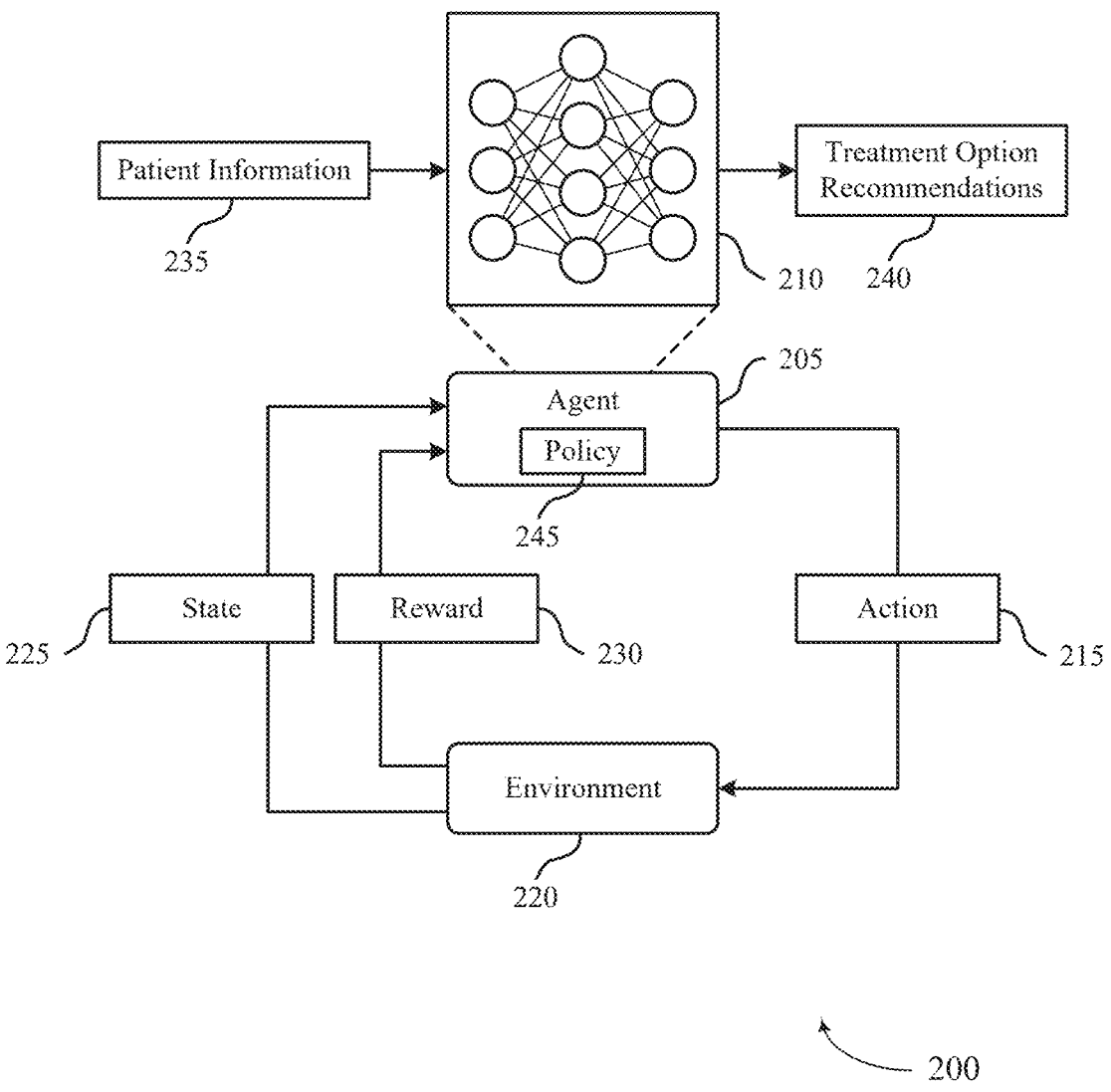
FIG. 2 shows an example of a reinforcement learning process for an AI model that supports treatment recommendations using genomic data in accordance with aspects of the present disclosure.

FIG. 2 shows an example of a reinforcement learning process 200 for an AI model 210 that supports treatment recommendations using genomic data in accordance with aspects of the present disclosure. A device, such as a processing device 110 or a user device 120 as described with reference to FIG. 1, may host the AI model 210 and perform the reinforcement learning process 200 to train the AI model 210. In some examples, the AI model 210 may be an example of the AI model 130 as described with reference to FIG. 1. The reinforcement learning process 200 may train the AI model 210 to recommend treatment options in response to a patient's genomic profile, the patient's treatment history, the patient's diagnosis, or any combination thereof.

The reinforcement learning process 200 may involve an agent 205 and an environment 220. The agent 205 may represent the AI model 210 (e.g., a machine learning (ML) algorithm or other AI component). The environment 220 may operate as an adaptive training space with attributes (e.g., variables, rules) that support optimization.

At a discrete time step, the agent 205 may select an action 215 from a set of supported actions to interact with the environment 220. In some examples, the agent 205 may select the action 215 based on a policy 245 (or policy map) that indicates probabilities of taking specific actions in accordance with a current state 225 of the environment 220. The agent 205 may send the selected action 215 to the environment 220. The device performing the reinforcement learning process 200 may perform the action 215 in or on the environment 220, such that the environment 220 may adapt from its current state to a new state 225 in response to the action 215. Additionally, the device performing the reinforcement learning process 200 may determine (or otherwise calculate) a reward 230 corresponding to the new state 225. The reward 230 may be a positive reward or a negative reward (e.g., a cost or penalty) associated with the transition from the current state of the environment 220 to the new state 225. The agent 205 may receive an indication of both of the new state 225 for the environment 220 and the reward 230. In some examples, the device may update the agent 205 (e.g., the policy 245 for the agent 205) in response to the reward 230. Additionally, or alternatively, the device may track a cumulative reward based on multiple rewards 230 determined at different discrete time steps. The device may repeat the process for any quantity of discrete time steps to iteratively train the agent 205. Following completion of the reinforcement learning process 200, the device may determine the AI model 210 for implementation that corresponds to the trained agent 205. In some examples, the device may retrain the agent 205 periodically, according to a schedule, or according to a trigger for retraining the agent 205.

In some cases, the AI model 210 may be an example of any reinforcement learning AI model. For example, the AI model 210 may be an example of a double DQN. A DQN may use deep Q-learning to train a policy 245 at the agent 205. For example, Q-learning may involve the device calculating a quality, or "Q value," for each pair of possible states 225 and possible actions 215. In some examples, the device may use a Q function to derive a new Q value, where the Q function is based on the previous Q value, a reward 230 for a specific action 215 taken at the previous state 225, and a maximum (or threshold) reward that can be obtained from the new state 225 after taking the action 215. Deep Q-learning may use relatively high-dimensional inputs and a pair of neural networks (e.g., an "online" neural network that is being trained and a "target" neural network) in place of relatively more simple Q functions to calculate the Q values. For example, the high-dimensional inputs may include one or more vectors indicating the state 225 of the environment 220. In some examples, the device may scale down the high-dimensional inputs to reduce a processing overhead associated with the reinforcement learning process 200. The high-dimensional inputs (or scaled versions of the high-dimensional inputs) may be sent through a convolutional neural network (e.g., the online neural network) that outputs a vector of Q values for each supported action. The device may update the online Q network (e.g., update weights of the online Q network) based on the current state, the new state, the action taken, the reward received, and the target Q network (e.g., weights of the target Q network). The device may refrain from updating the target Q network, or may update the target Q network at relatively longer intervals as compared to the online Q network updates.

Double DQN may at least partially decouple action 215 selection from action 215 evaluation for the deep Q-learning process by using the different neural networks (e.g., the online neural network and the target neural network) for different tasks. For example, the device may update the policy 245 at the agent 205 using the online neural network but may evaluate the updated policy 245 using the target neural network. This decoupling may reduce over-estimation of Q values and improve the accuracy of the resulting policy 245 at the agent 205.

The device may train the AI model 210 to output accurate treatment option recommendations 240 in response to patient information 235. The device may use patient similarities and patient journeys as ground truths to determine the rewards 230 for updating the policy 245 and training the AI model 210. In some examples, the device may use data from medical providers, insurance providers, genomic researchers, or any combination thereof to train the AI model 210. The data may be de-identified data linked to social determinants of health. The agent 205 may recommend an action 215, such as a next treatment in a patient's journey, based on the current state 225 of the environment 220. The device may use other patients with similar journeys to determine if this action 215 (e.g., this recommended next treatment) is predicted to improve the patient's health, have no effect, or harm the patient's health. The device may apply a significant cost for any recommended treatment predicted to harm the patient's health, a relatively smaller cost for any recommended treatment predicted to have no effect on the patient's health, or a positive reward for any recommended treatment predicted to have a positive effect on the patient's health. In some cases, as patients return with treatment results (e.g., whether the recommend treatments were effective for the patients), the device may retrain the AI model 210 using the patient results as feedback to continue improving the AI model 210.

Using the reinforcement learning process 200 in the context of treatment recommendations may potentially result in dangerous treatment recommendations. For example, because the reinforcement learning process 200 trains the AI model 210 based on similar patients and patient journeys, the AI model 210 may fail to identify that relatively small differences between patients may have significant differences in what treatments can be prescribed. For example, a first patient may include a genetic marker that indicates they are allergic to a specific drug. However, a second patient with a similar patient journey to the first patient, but who does not have this genetic marker, may respond very positively to the specific drug. Accordingly, the reinforcement learning process 200 may reward the policy 245 for recommending a treatment involving this drug for the first patient. Because the reinforcement learning process 200 may not allow for a user to define strict rules or manually modify weights of the AI model 210, the reinforcement learning process 200 may fail to protect patients from such dangerous treatment recommendations.

The system 100 may solve this potential problem with the reinforcement learning process 200 by implementing a rules-based engine (e.g., the rules-based engine 125) with the AI model trained via the reinforcement learning process 200 (e.g., the AI model 130). The rules-based engine may set strict rules that define whether a genetic marker for a patient disqualifies using a specific drug. Such strict rules may be used on the outputs of the AI model (e.g., the AI model 210) to modify or remove one or more treatment option recommendations 240 to mitigate any potentially dangerous treatment recommendations. Accordingly, the system 100 may leverage the combination of the rules-based engine 125 and the AI model 130 to mitigate a potential technical deficiency of reinforcement learning in the specific context of medical treatment recommendation for patients (e.g., a potential technical deficiency that may not affect other contexts for reinforcement learning that cannot jeopardize patient health).

In various implementations, the models and/or modules described herein (e.g., including, but not limited to, the AI model 210) may be classification, predictive, generative, conversational, reinforcement learning, or another form of AI technology, such as AI model(s), agents, etc., implementing one or more forms of machine learning, neural networks, statistical modeling, deep learning, automation, natural language processing, or other similar technology. The AI technology may be included as part of a network or system comprising a hardware- or software-based framework for training, processing, fine-tuning, or performing any other implementation steps. Furthermore, the AI technology may include a hardware- or software-based framework that performs one or more functions, such as retrieving, generating, accessing, transmitting, etc. The AI technology may be implemented by a computer including a register coupled with a processor or a central processing unit (CPU).

Moreover, the AI technology may be trained or fine-tuned using supervised, unsupervised, or other AI training techniques. In various implementations, the AI technology may be trained or fine-tuned using a set of general datasets or a set of datasets directed to a particular field or task. Additionally, or alternatively, the AI technology may be intermittently updated at a set interval or in real time based on resulting output or additional data to further train the AI technology. The AI technology may offer a variety of capabilities including text, audio, image, and other content generation, translation, summarization, classification, prediction, recommendation, time-series forecasting, searching, matching, pairing, and more. These capabilities may be provided in the form of output produced by the AI technology in response to a particular prompt or other input. Furthermore, the AI technology may implement Retrieval-Augmented Generation (RAG) or other techniques after training or fine-tuning by accessing a set of documents or knowledge base directed to a particular field or website other than the training or fine-tuning data to influence the AI technology's output with the set of documents or knowledge base.

To further guide and train output of the AI technology, one or more input prompts may be provided to the AI technology for the purpose of eliciting particular responses. In various implementations, the input prompts may correspond to the particular field or task to which the AI technology is trained. Additionally, or alternatively, the AI technology may be implemented along with one or more additional AI technologies. For example, a first AI model may produce a first output, which is used as input for a second AI model to produce a second output. These AI technologies may be used in succession of one another, in parallel with another, or a combination of both. Furthermore, the AI technologies may be merged in a variety of implementations, for example, by bagging, boosting, stacking, etc. the AI technologies.

Figure 3:
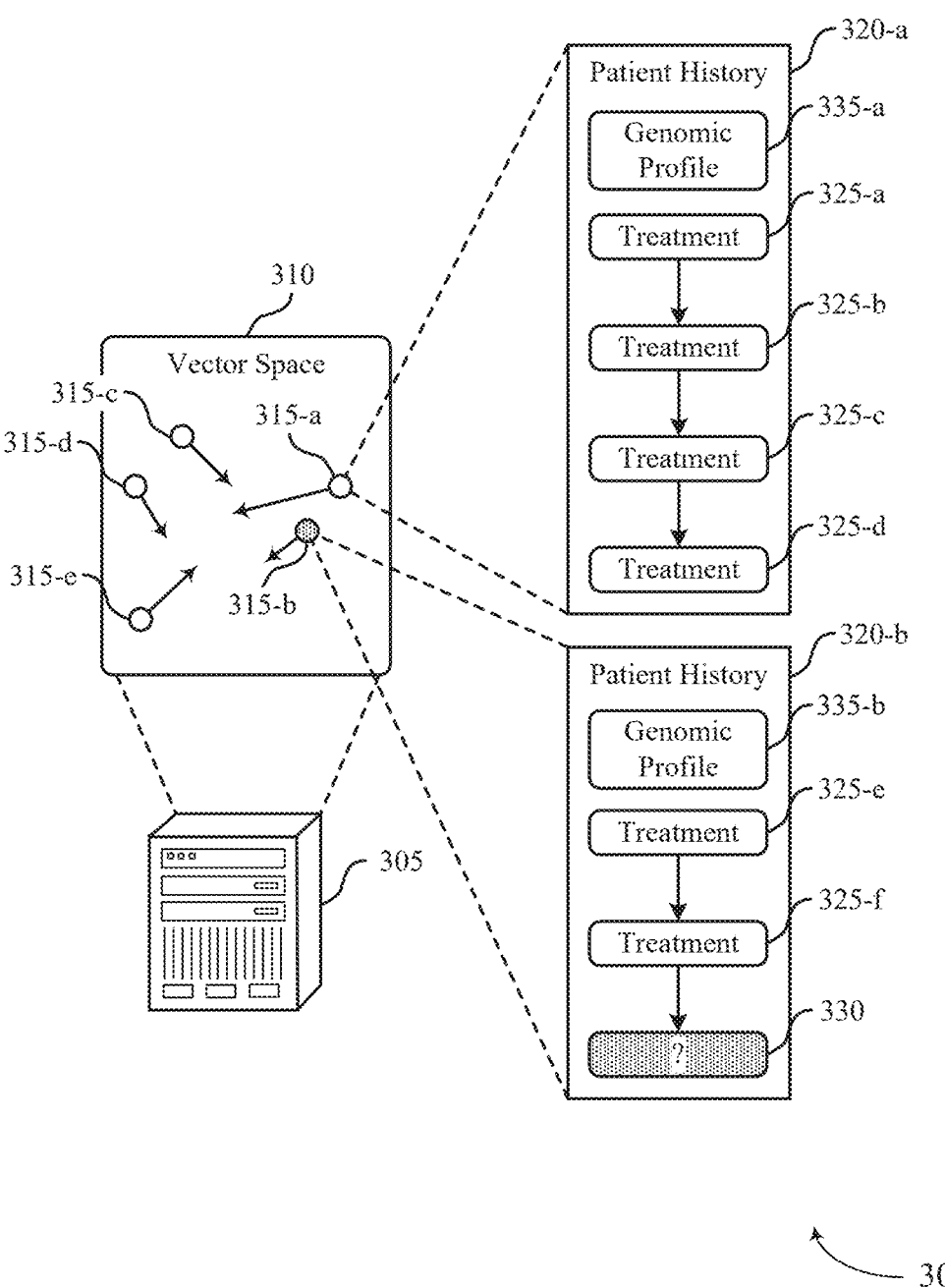
FIG. 3 shows an example of a patient similarity analysis using vector mapping that supports treatment recommendations using genomic data and reinforcement learning in accordance with aspects of the present disclosure.

FIG. 3 shows an example of a patient similarity analysis 300 using vector mapping that supports treatment recommendations using genomic data and reinforcement learning in accordance with aspects of the present disclosure. In some examples, a device 305, such as a processing device 110 or a user device 120 as described with reference to FIG. 1, may use the patient similarity analysis 300 to support reinforcement learning, such as the reinforcement learning process 200 described with reference to FIG. 2. For example, the device 305 may use vector similarities of patients to determine rewards for training an AI model, such as the AI model 130 or the AI model 210 as described with reference to FIGS. 1 and 2.

The device 305 may host a vector space 310. The device 305 may map patient information to vectors in the vector space 310. In some examples, the vector space 310 may be specific to a diagnosis or condition for patients, such that all of the vectors in the vector space correspond to patients with the same diagnosis or condition. The vectors may be n-dimensional vectors of any value n; that is, the vector space 310 may support vectors with any quantity of dimensions. Each vector may represent information (e.g., a patient history) for one patient, such as a genomic profile of the patient, a treatment history of the patient, other social determinants of health, or any combination thereof. In some cases, to ensure secure handling of medical records, the patient history may not include any PII for the patient.

The device 305 may determine patient similarities using the vectors in the vector space 310. For example, the vector space 310 may include any quantity of vectors representing any quantity of patients, such as a first vector 315-*a* representing a first patient, a second vector 315-*b* representing a second patient, a third vector 315-*c* representing a third patient, a fourth vector 315-*d* representing a fourth patient, and a fifth vector 315-*c* representing a fifth patient. In some examples, multiple vectors may represent the same patient at different stages in their treatment history. For example, because the patient histories may refrain from including PII, the device 305 may fail to determine whether a vector in the vector space 310 corresponds to the same patient as another vector in the vector space 310.

As illustrated in FIG. 3, the vector 315-*a* may represent a patient history 320-*a* for a first patient. The patient history 320-*a* may include a first set of treatments (and an order of the first set of treatments) prescribed to the first patient, a genomic profile 335-*a* of the first patient, or both. For example, the treatment history for the first patient may include a first treatment 325-*a*, a second treatment 325-*b*, a third treatment 325-*c*, and a fourth treatment 325-*d*. Additionally, the vector 315-*b* may represent a patient history 320-*b* for a second patient, such as a patient being analyzed for a recommendation of a next treatment 330. The patient history 320-*b* may include a second set of treatments (and an order of the second set of treatments) prescribed to the second patient, a genomic profile 335-*b* of the second patient, or both. For example, the treatment history for the second patient may include a first treatment 325-*e* and a second treatment 325-*f*. The device 305 may use, in part, patient similarity analysis to recommend a next treatment 330 for the second patient. For example, the device 305 may determine to recommend a next treatment 330 that was helpful to patients that are relatively similar to the second patient according to a vector similarity in the vector space. The device 305 may calculate vector similarity (e.g., corresponding to patient similarity) using a cosine similarity calculation, a Euclidean distance calculation between vectors, or another vector similarity function. In some examples, the vector space 310, the vector similarity function, or both may weight the similarity calculation between a treatment history similarity and a genomic profile similarity according to the specific diagnosis or condition for the vector space 310. For example, treatment history similarity may be relatively more significant for some conditions, while genomic profile (or other patient information) may be relatively more significant for some other conditions.

As an example, the device 305 may determine that vector 315-*b* is relatively close to vector 315-*a* based on a cosine similarity. For example, the cosine similarity may satisfy a threshold distance. The second patient corresponding to vector 315-*b* may have a relatively similar genomic profile, treatment history, or both as compared to the first patient corresponding to vector 315-*a*. For example, both patients may have been assigned a same (or relatively similar) first treatment (e.g., the treatment 325-*a* and the treatment 325-*c*) and a same (or relatively similar) second treatment (e.g., the treatment 325-*b* and the treatment 325-*f*). The first patient may have additionally been prescribed a third treatment 325-*c* that did not improve the patient's health and a fourth treatment 325-*d* that did improve the patient's health. Accordingly, determining a next treatment 330 recommendation for the second patient may be rewarded at least in part based on the effects on the first patient's health. For example, the device 305 may assign a cost to recommending the third treatment 325-*c* as the next treatment 330 for the second patient based on the similarity with the first patient and the third treatment 325-*c* negatively affecting the first patient's health. In contrast, the device 305 may assign a reward to recommending the fourth treatment 325-*d* as the next treatment 330 for the second patient based on the similarity with the first patient and the fourth treatment 325-*d* positively affecting the first patient's health. Accordingly, the AI model trained using such a reward system (e.g., using the vector similarities) may be more likely to recommend, as the next treatment 330 for the second patient, the fourth treatment 325-*d* rather than the third treatment 325-*c*. Accordingly, the AI model may effectively diverge the treatment histories for these patients to improve the likelihood that the second patient is receiving a beneficial treatment at an earlier date, learning from the first patient's treatment history. That is, using the patient similarity analysis 300, the device 305 may train an AI model that predicts optimal courses of treatment for each patient.

The patient similarity analysis 300 may support complex patient journeys (e.g., treatment histories). For example, treatment efficacy may decrease over time for some conditions, such as for HIV. Determining if a treatment is effective for HIV may involve two metrics: viral load and patient health. The treatment may be helpful if it causes a patient's viral load to decrease and health to increase. The rewards used for similar HIV patients may involve tradeoffs between viral load, patient health, and time (e.g., if the treatment becomes less effective over time). The rewards may depend on multiple similar patients (e.g., a group of similar patients corresponding to vectors within a threshold distance from each other).

Figure 4:
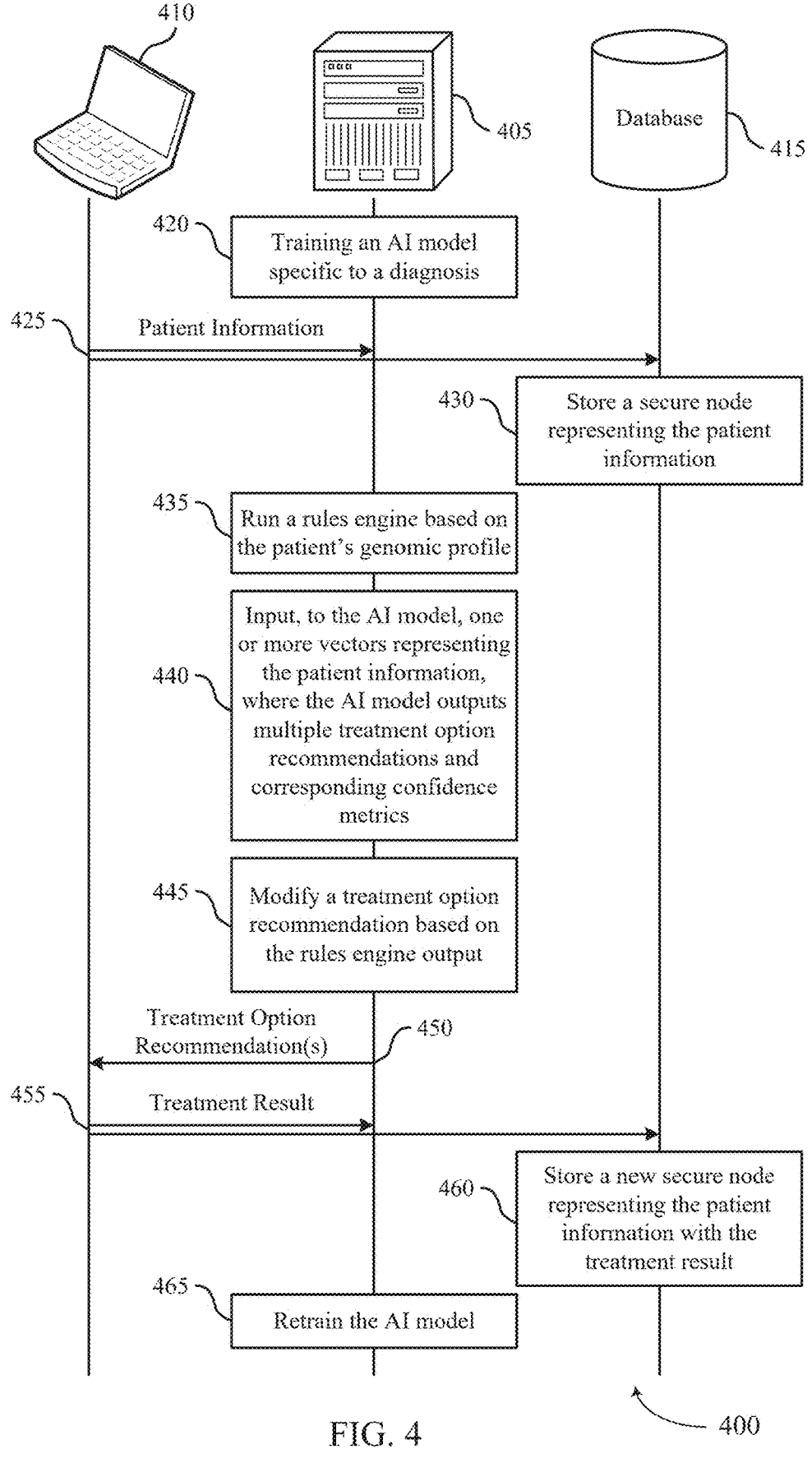
FIG. 4 shows an example of a process flow that supports treatment recommendations using genomic data and reinforcement learning in accordance with aspects of the present disclosure.

FIG. 4 shows an example of a process flow 400 that supports treatment recommendations using genomic data and reinforcement learning in accordance with aspects of the present disclosure. The process flow 400 may include a processing device 405, a user device 410, and a database 415. The processing device 405 may be an example of a processing device 110 or a device 305 as described with reference to FIGS. 1 and 3. The user device 410 may be an example of a user device 120 as described with reference to FIG. 1, and the database 415 may be an example of a database 115 as described with reference to FIG. 1. The processing device 405 may support AI techniques to determine treatment recommendations based on genomic data associated with patients. In the following description of the process flow 400, the operations may be performed in a different order than is shown. Some operations may be omitted from the process flow 400, and some other operations may be added to the process flow 400. Further, although some operations may be shown to occur at different times for discussion purposes, these operations may occur at the same time. Additionally, or alternatively, other devices may perform aspects of the process flow 400.

At 420, the processing device 405 may train an AI model using reinforcement learning. In some examples, the processing device 405 may train multiple AI models, where each AI model corresponds to a specific diagnosis (e.g., a specific medical condition). For example, the processing device 405 may train a reinforcement learning AI model for a diagnosis based on a corpus of data for a set of users (e.g., a set of patients with the same diagnosis). The corpus of data may include respective genomic profiles, treatment histories, treatment results, or a combination thereof for the users.

In some examples, training the AI model may involve using one or more training vectors indicating a set of training data from the corpus of data, the set of training data including a respective genomic profile and a respective treatment history for a respective user. The processing device 405 may embed patient information into a vector space and use vector closeness (e.g., vector similarity) to measure patient similarity. The processing device 405 may apply cost values, reward values, or both to the reinforcement learning AI model according to the patient similarities and treatment results for the relatively similar patients. In some cases, the AI model may be an example of a double DQN.

At 425, the processing device 405 may receive, for a user (e.g., a patient), data indicating at least a diagnosis, a genomic profile, and a treatment history. In some examples, the data may include other patient information. The genomic profile may be a full genetic sequencing for the user (e.g., the patient), a partial genetic sequencing for the user, a set of biomarkers for the user, or any combination of these or other information indicating genomic data for the user. The treatment history may include a set of treatments previously prescribed to the user, an order of the treatments, results of the treatments, or any combination thereof. In some examples, the processing device 405 may receive the data from a user device 410. For example, the patient, a doctor or other healthcare professional working with the patient, or an insurance company representative working with the patient may trigger the data being sent to the processing device 405 for analysis. In some examples, the user device 410 may additionally send the data to a database 415 for storage. The database 415 may be an example of a secure database, such as a graph database or document database implementing encryption at rest.

At 430, the database 415 may store a secure node representing the patient data (e.g., the diagnosis, the genomic profile, the treatment history, or a combination thereof for the user). The database 415 may refrain from storing any PII for the patient with the secure node.

At 435, the processing device 405 may run a rules engine (e.g., a rules-based engine) based on the genomic profile to determine any relevant treatment modifications for the user (e.g., the patient). For example, the rules engine may map specific biomarkers to rules based on drug responses corresponding to the biomarkers. For example, one or more biomarkers indicated by the genomic profile may correspond—or otherwise correlate—to drug responses, such as drug allergies, drug metabolism, drug absorption, or any other responses. In some cases, the rules engine may output one or more treatment modifications. In some other cases, the rules engine may not output any treatment modifications, indicating no treatment modifications based on the user's genomic profile.

At 440, the processing device 405 may input, to the AI model trained at 420, one or more vectors indicating the diagnosis, the genomic profile, and the treatment history. In some examples, the processing device 405 may select the AI model to use based on the diagnosis and may input one or more vectors representing the genomic profile and the treatment history to the selected AI model. The AI model may output, in response to the one or more vectors, a set of treatment option recommendations and corresponding confidence metrics. In some examples, the AI model may output one treatment option recommendation (e.g., the one corresponding to a greatest confidence metric). In some other examples, the AI model may output multiple treatment option recommendations with respective confidence metrics.

In some examples, at 445, the processing device 405 may modify one or more treatment option recommendations based on the output (e.g., one or more treatment modifications) of the rules engine at 435. In some cases, the processing device 405 may remove a treatment option recommendation from the set of treatment option recommendations, modify a drug dosage recommendation (or other recommendation, such as a schedule) for a treatment option recommendation, remove a drug combination from a treatment option recommendation, or any combination thereof.

At 450, the processing device 405 may output, to a user interface of the user device 410, the set of treatment option recommendations for display. In some cases, the processing device 405 may additionally send the corresponding confidence metrics for display or other information relating to the treatment option recommendations. The treatment option recommendations sent to the user device 410 may be the modified treatment option recommendations based on the rules engine at 445.

At 455, the processing device 405, the database 415, or both may receive treatment results for the user (e.g., the patient) based on the set of treatment option recommendations. For example, the user may be prescribed one treatment (e.g., the treatment corresponding to the highest confidence metric) and may follow up with corresponding results on their health (e.g., if the treatment positively or negatively affected the user). At 460, the database 415 may store a new secure node representing the patient data updated with the latest treatment results (e.g., the diagnosis, the genomic profile, the treatment history with the prescribed treatment and corresponding results, or a combination thereof for the user). In some cases, at 465, the processing device 405 may retrain the AI model based on the treatment results.

Figure 5:
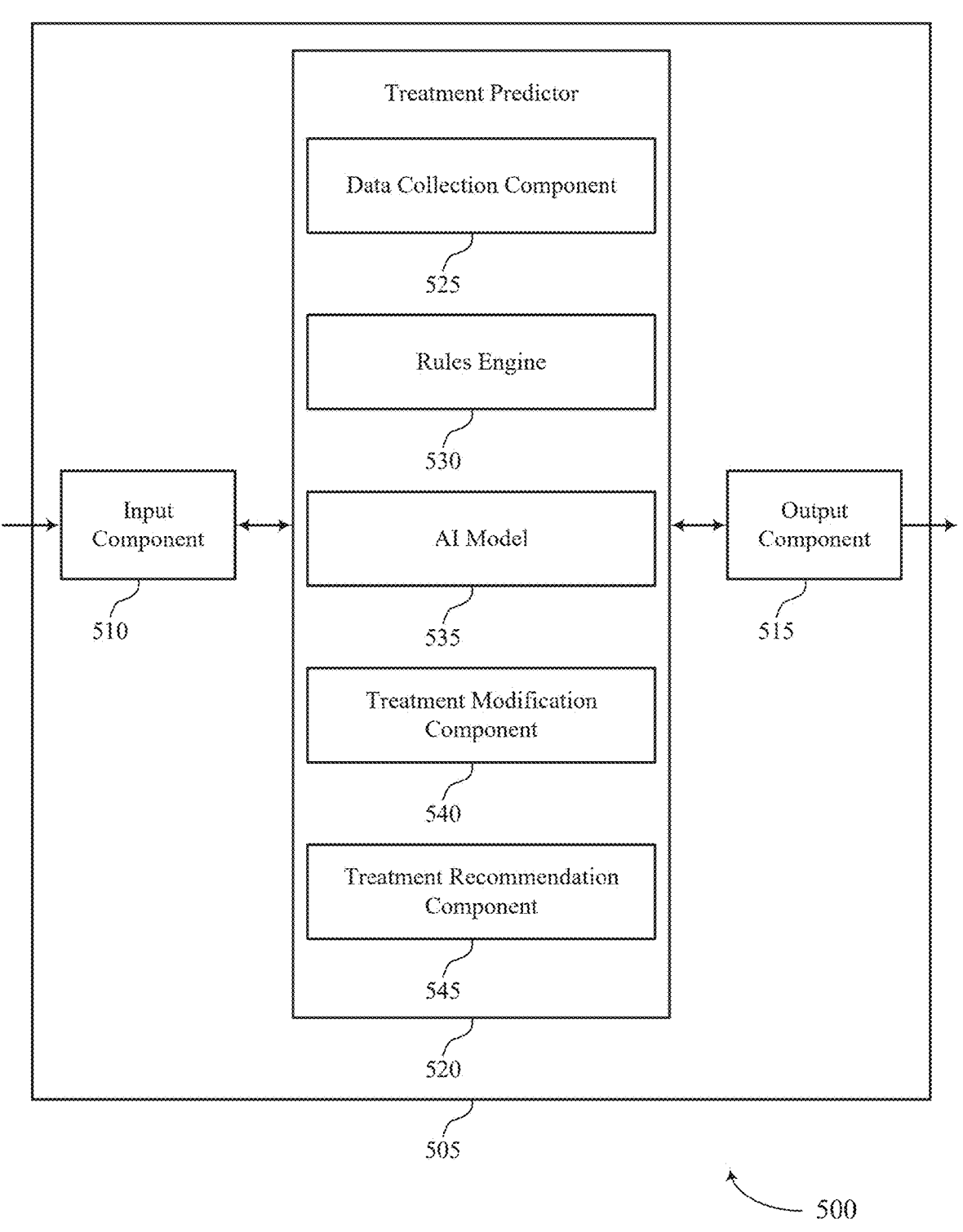
FIG. 5 shows a block diagram of a device that supports treatment recommendations using genomic data and reinforcement learning in accordance with aspects of the present disclosure.

FIG. 5 shows a block diagram 500 of a device 505 that supports treatment recommendations using genomic data and reinforcement learning in accordance with aspects of the present disclosure. The device 505 may include an input component 510, an output component 515, and a treatment predictor 520. The device 505, or one of more components of the device 505 (e.g., the input component 510, the output component 515, the treatment predictor 520), may include at least one processor, which may be coupled with at least one memory, to support the described techniques. Each of these components may be in communication with one another (e.g., via one or more buses).

The input component 510 may manage input signals for the device 505. For example, the input component 510 may identify input signals based on an interaction with a modem, a keyboard, a mouse, a touchscreen, or a similar device. These input signals may be associated with user input or processing at other components or devices. In some cases, the input component 510 may utilize an operating system such as iOS®, ANDROID®, MS-DOS®, MS-WINDOWS®, OS/2®, UNIX®, LINUX®, or another known operating system to handle input signals. The input component 510 may send aspects of these input signals to other components of the device 505 for processing. For example, the input component 510 may transmit input signals to the treatment predictor 520 to support treatment recommendations using genomic data and reinforcement learning. In some cases, the input component 510 may be a component of an input/output (I/O) controller 710 as described with reference to FIG. 7.

The output component 515 may manage output signals for the device 505. For example, the output component 515 may receive signals from other components of the device 505, such as the treatment predictor 520, and may transmit these signals to other components or devices. In some examples, the output component 515 may transmit output signals for display in a user interface, for storage in a database or data store, for further processing at a server or server cluster, or for any other processes at any number of devices or systems. In some cases, the output component 515 may be a component of an I/O controller 710 as described with reference to FIG. 7.

For example, the treatment predictor 520 may include a data collection component 525, a rules engine 530, an AI model 535, a treatment modification component 540, a treatment recommendation component 545, or any combination thereof. In some examples, the treatment predictor 520, or various components thereof, may be configured to perform various operations (e.g., receiving, monitoring, transmitting) using or otherwise in cooperation with the input component 510, the output component 515, or both. For example, the treatment predictor 520 may receive information from the input component 510, send information to the output component 515, or be integrated in combination with the input component 510, the output component 515, or both to receive information, transmit information, or perform various other operations as described herein.

The treatment predictor 520 may support recommending treatment options in accordance with examples as disclosed herein. The data collection component 525 may be configured to support receiving, for a user, data indicating a diagnosis, a genomic profile, and a treatment history. The rules engine 530 may be configured to support running a rules engine based on the genomic profile to determine one or more treatment modifications for the user. The AI model 535 may be configured to support inputting, to a reinforcement learning AI model, one or more vectors indicating the diagnosis, the genomic profile, and the treatment history, where the reinforcement learning AI model outputs, in response to the one or more vectors, a set of multiple treatment option recommendations and a set of multiple confidence metrics, where a respective confidence metric corresponds to a respective treatment option recommendation. The treatment modification component 540 may be configured to support modifying at least one treatment option recommendation of the set of multiple treatment option recommendations based on the one or more treatment modifications for the user. The treatment recommendation component 545 may be configured to support outputting, to a user interface of a user device, the set of multiple treatment option recommendations and the set of multiple confidence metrics based on the at least one modified treatment option recommendation.

Figure 6:
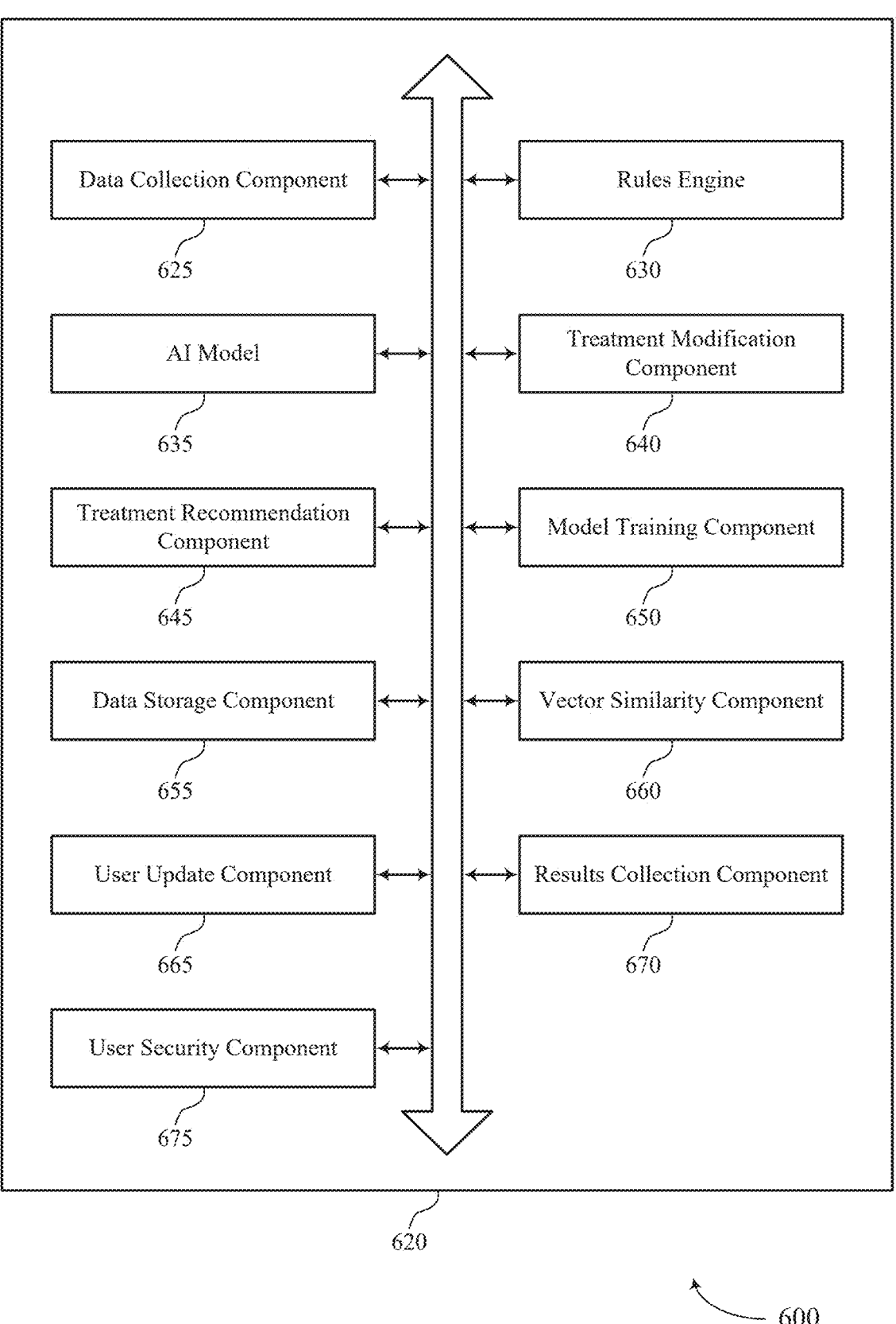
FIG. 6 shows a block diagram of a treatment predictor that supports treatment recommendations using genomic data and reinforcement learning in accordance with aspects of the present disclosure.

FIG. 6 shows a block diagram 600 of a treatment predictor 620 that supports treatment recommendations using genomic data and reinforcement learning in accordance with aspects of the present disclosure. The treatment predictor 620 may be an example of aspects of a treatment predictor 520 as described herein. The treatment predictor 620, or various components thereof, may be an example of means for performing various aspects of treatment recommendations using genomic data and reinforcement learning as described herein. For example, the treatment predictor 620 may include a data collection component 625, a rules engine 630, an AI model 635, a treatment modification component 640, a treatment recommendation component 645, a model training component 650, a data storage component 655, a vector similarity component 660, a user update component 665, a results collection component 670, a user security component 675, or any combination thereof. Each of these components, or components of subcomponents thereof (e.g., one or more processors, one or more memories), may communicate, directly or indirectly, with one another (e.g., via one or more buses).

The treatment predictor 620 may support recommending treatment options in accordance with examples as disclosed herein. The data collection component 625 may be configured to support receiving, for a user, data indicating a diagnosis, a genomic profile, and a treatment history. The rules engine 630 may be configured to support running a rules engine based on the genomic profile to determine one or more treatment modifications for the user. The AI model 635 may be configured to support inputting, to a reinforcement learning AI model, one or more vectors indicating the diagnosis, the genomic profile, and the treatment history, where the reinforcement learning AI model outputs, in response to the one or more vectors, a set of multiple treatment option recommendations and a set of multiple confidence metrics, where a respective confidence metric corresponds to a respective treatment option recommendation. The treatment modification component 640 may be configured to support modifying at least one treatment option recommendation of the set of multiple treatment option recommendations based on the one or more treatment modifications for the user. The treatment recommendation component 645 may be configured to support outputting, to a user interface of a user device, the set of multiple treatment option recommendations and the set of multiple confidence metrics based on the at least one modified treatment option recommendation.

In some examples, the model training component 650 may be configured to support training the reinforcement learning AI model for the diagnosis based on a corpus of data for a set of multiple users, the corpus of data including a set of multiple respective genomic profiles, a set of multiple respective treatment histories, and a set of multiple respective results for the set of multiple users. In some examples, to support training the reinforcement learning AI model, the model training component 650 may be configured to support inputting, to the reinforcement learning AI model, one or more training vectors indicating a set of training data from the corpus of data, the set of training data including a respective genomic profile and a respective treatment history for a respective user, where the reinforcement learning AI model outputs, in response to the one or more training vectors, a treatment option recommendation for the respective user. In some examples, to support training the reinforcement learning AI model, the model training component 650 may be configured to support applying a cost value or a reward value to the reinforcement learning AI model based on the corpus of data indicating a result of a treatment corresponding to the treatment option recommendation for the respective user.

In some examples, the results collection component 670 may be configured to support receiving a result of a treatment for the user based on a treatment option recommendation for the set of multiple treatment option recommendations. In some examples, the model training component 650 may be configured to support retraining the reinforcement learning AI model for the diagnosis based on the result of the treatment for the user.

In some examples, the reinforcement learning AI model is trained specific to the diagnosis, and the model training component 650 may be configured to support training a second reinforcement learning AI model specific to a second diagnosis different from the diagnosis.

In some examples, the data storage component 655 may be configured to support storing, in a database, a secure node representing the diagnosis, the genomic profile, and the treatment history for the user. In some examples, the results collection component 670 may be configured to support receiving a result of a treatment for the user based on a treatment option recommendation for the set of multiple treatment option recommendations, where the treatment history for the user is updated based on the result of the treatment for the user. In some examples, the data storage component 655 may be configured to support storing, in the database, an additional secure node representing the diagnosis, the genomic profile, and the treatment history for the user updated based on the result of the treatment for the user.

In some examples, the vector similarity component 660 may be configured to support generating a vector representing the user based on the diagnosis, the genomic profile, the treatment history, or a combination thereof. In some examples, the vector similarity component 660 may be configured to support determining one or more other users similar to the user based on a vector similarity test for the vector representing the user and one or more other vectors representing the one or more other users in a vector space, where the set of multiple treatment option recommendations is based on the one or more other users similar to the user.

In some examples, to support modifying the at least one treatment option recommendation, the treatment modification component 640 may be configured to support removing a first treatment option recommendation from the set of multiple treatment option recommendations based on the one or more treatment modifications for the user, modifying a drug dosage recommendation for a second treatment option recommendation of the set of multiple treatment option recommendations based on the one or more treatment modifications for the user, removing a drug combination from a third treatment option recommendation of the set of multiple treatment option recommendations based on the one or more treatment modifications for the user, or any combination thereof.

In some examples, the one or more vectors input to the reinforcement learning AI model further indicate at least one treatment modification of the one or more treatment modifications for the user.

In some examples, the user update component 665 may be configured to support receiving, via the user interface of the user device, a user input indicating an update to a treatment option recommendation of the set of multiple treatment option recommendations. In some examples, the user update component 665 may be configured to support inputting, to the reinforcement learning AI model, one or more additional vectors indicating the diagnosis, the genomic profile, the treatment history, and the update to the treatment option recommendation, where the reinforcement learning AI model outputs, in response to the one or more additional vectors, an updated set of multiple treatment option recommendations and an updated set of multiple confidence metrics, where a respective updated confidence metric corresponds to a respective updated treatment option recommendation. In some examples, the treatment recommendation component 645 may be configured to support outputting, to the user interface of the user device, the updated set of multiple treatment option recommendations and the updated set of multiple confidence metrics.

In some examples, the genomic profile includes a full genetic sequencing for the user, a set of biomarkers for the user, or both. In some examples, the reinforcement learning AI model includes a Double DQN.

In some examples, the treatment recommendation component 645 may be configured to support outputting, to a system (e.g., an insurance system), a first treatment option recommendation of the set of multiple treatment option recommendations that corresponds to a first confidence metric satisfying a confidence threshold. In some examples, the user security component 675 may be configured to support refraining from outputting, to the system, the genomic profile, the treatment history, or both for the user.

Figure 7:
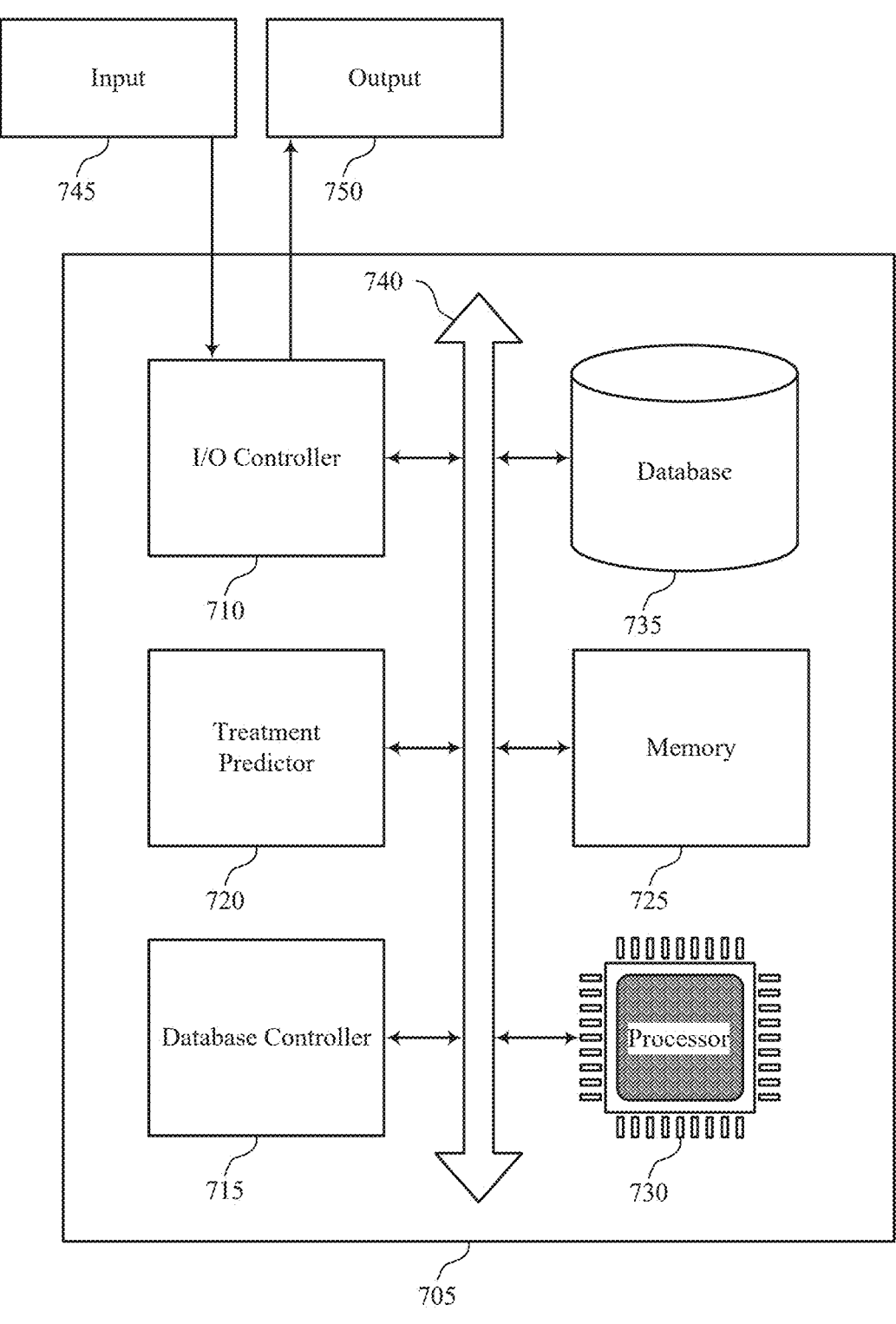
FIG. 7 shows a diagram of a system including a device that supports treatment recommendations using genomic data and reinforcement learning in accordance with aspects of the present disclosure.

FIG. 7 shows a diagram of a system 700 including a device 705 that supports treatment recommendations using genomic data and reinforcement learning in accordance with aspects of the present disclosure. The device 705 may be an example of or include components of a device 505 as described herein. The device 705 may include components for bi-directional data communications including components for transmitting and receiving communications, such as a treatment predictor 720, an I/O controller, such as an I/O controller 710, a database controller 715, at least one memory 725, at least one processor 730, and a database 735. These components may be in electronic communication or otherwise coupled (e.g., operatively, communicatively, functionally, electronically, electrically) via one or more buses (e.g., a bus 740).

The I/O controller 710 may manage input signals 745 and output signals 750 for the device 705. The I/O controller 710 may also manage peripherals not integrated into the device 705. In some cases, the I/O controller 710 may represent a physical connection or port to an external peripheral. In some cases, the I/O controller 710 may utilize an operating system such as iOS®, ANDROID®, MS-DOS®, MS-WIN- DOWS®, OS/2®, UNIX®, LINUX®, or another known operating system. In other cases, the I/O controller 710 may represent or interact with a modem, a keyboard, a mouse, a touchscreen, or a similar device. In some cases, the I/O controller 710 may be implemented as part of a processor 730. In some examples, a user may interact with the device 705 via the I/O controller 710 or via hardware components controlled by the I/O controller 710.

The database controller 715 may manage data storage and processing in a database 735. In some cases, a user may interact with the database controller 715. In other cases, the database controller 715 may operate automatically without user interaction. The database 735 may be an example of a single database, a distributed database, multiple distributed databases, a data store, a data lake, or an emergency backup database.

Memory 725 may include random-access memory (RAM) and read-only memory (ROM). The memory 725 may store computer-readable, computer-executable software including instructions that, when executed, cause at least one processor 730 to perform various functions described herein. In some cases, the memory 725 may contain, among other things, a basic I/O system (BIOS) which may control basic hardware or software operation such as the interaction with peripheral components or devices. The memory 725 may be an example of a single memory or multiple memories. For example, the device 705 may include one or more memories 725.

The processor 730 may include an intelligent hardware device (e.g., a general-purpose processor, a digital signal processor (DSP), a CPU, a microcontroller, an application-specific integrated circuit (ASIC), a field-programmable gate array (FPGA), a programmable logic device, a discrete gate or transistor logic component, a discrete hardware component, or any combination thereof). In some cases, the processor 730 may be configured to operate a memory array using a memory controller. In other cases, a memory controller may be integrated into the processor 730. The processor 730 may be configured to execute computer-readable instructions stored in at least one memory 725 to perform various functions (e.g., functions or tasks supporting treatment recommendations using genomic data and reinforcement learning). The processor 730 may be an example of a single processor or multiple processors. For example, the device 705 may include one or more processors 730.

The treatment predictor 720 may support recommending treatment options in accordance with examples as disclosed herein. For example, the treatment predictor 720 may be configured to support receiving, for a user, data indicating a diagnosis, a genomic profile, and a treatment history. The treatment predictor 720 may be configured to support running a rules engine based on the genomic profile to determine one or more treatment modifications for the user. The treatment predictor 720 may be configured to support inputting, to a reinforcement learning AI model, one or more vectors indicating the diagnosis, the genomic profile, and the treatment history, where the reinforcement learning AI model outputs, in response to the one or more vectors, a set of multiple treatment option recommendations and a set of multiple confidence metrics, where a respective confidence metric corresponds to a respective treatment option recommendation. The treatment predictor 720 may be configured to support modifying at least one treatment option recommendation of the set of multiple treatment option recommendations based on the one or more treatment modifications for the user. The treatment predictor 720 may be configured to support outputting, to a user interface of a user device, the set of multiple treatment option recommendations and the set of multiple confidence metrics based on the at least one modified treatment option recommendation.

FIG. 8 shows a flowchart illustrating a method 800 that supports treatment recommendations using genomic data and reinforcement learning in accordance with aspects of the present disclosure. The operations of the method 800 may be implemented by a processing device or its components as described herein. For example, the operations of the method 800 may be performed by a processing device or system, such as an application server, a database server, a cloud-based server or service, a worker server, a server cluster, a virtual machine, a container, a network device, a user device, or any combination of these or other computing devices. In some examples, a processing device or system may execute a set of instructions to control the functional elements of the processing device or system to perform the described functions. Additionally, or alternatively, the processing device or system may perform aspects of the described functions using special-purpose hardware.

At 805, the method may include receiving, for a user, data indicating a diagnosis, a genomic profile, and a treatment history. The operations of 805 may be performed in accordance with examples as disclosed herein. In some examples, aspects of the operations of 805 may be performed by a data collection component 625 as described with reference to FIG. 6.

At 810, the method may include running a rules engine based on the genomic profile to determine one or more treatment modifications for the user. The operations of 810 may be performed in accordance with examples as disclosed herein. In some examples, aspects of the operations of 810 may be performed by a rules engine 630 as described with reference to FIG. 6.

At 815, the method may include inputting, to a reinforcement learning AI model, one or more vectors indicating the diagnosis, the genomic profile, and the treatment history, where the reinforcement learning AI model outputs, in response to the one or more vectors, a set of multiple treatment option recommendations and a set of multiple confidence metrics, where a respective confidence metric corresponds to a respective treatment option recommendation. The operations of 815 may be performed in accordance with examples as disclosed herein. In some examples, aspects of the operations of 815 may be performed by an AI model 635 as described with reference to FIG. 6.

At 820, the method may include modifying at least one treatment option recommendation of the set of multiple treatment option recommendations based on the one or more treatment modifications for the user. The operations of 820 may be performed in accordance with examples as disclosed herein. In some examples, aspects of the operations of 820 may be performed by a treatment modification component 640 as described with reference to FIG. 6.

At 825, the method may include outputting, to a user interface of a user device, the set of multiple treatment option recommendations and the set of multiple confidence metrics based on the at least one modified treatment option recommendation. The operations of 825 may be performed in accordance with examples as disclosed herein. In some examples, aspects of the operations of 825 may be performed by a treatment recommendation component 645 as described with reference to FIG. 6.

FIG. 9 shows a flowchart illustrating a method 900 that supports treatment recommendations using genomic data and reinforcement learning in accordance with aspects of the present disclosure. The operations of the method 900 may be implemented by a processing device or its components as described herein. For example, the operations of the method 900 may be performed by a processing device or system, such as an application server, a database server, a cloud-based server or service, a worker server, a server cluster, a virtual machine, a container, a network device, a user device, or any combination of these or other computing devices. In some examples, a processing device or system may execute a set of instructions to control the functional elements of the processing device or system to perform the described functions. Additionally, or alternatively, the processing device or system may perform aspects of the described functions using special-purpose hardware.

At 905, the method may include training a reinforcement learning AI model for a diagnosis based on a corpus of data for a set of multiple users, the corpus of data including a set of multiple respective genomic profiles, a set of multiple respective treatment histories, and a set of multiple respective results for the set of multiple users. The operations of 905 may be performed in accordance with examples as disclosed herein. In some examples, aspects of the operations of 905 may be performed by a model training component 650 as described with reference to FIG. 6.

At 910, the method may include inputting, to the reinforcement learning AI model, one or more training vectors indicating a set of training data from the corpus of data, the set of training data including a respective genomic profile and a respective treatment history for a respective user, where the reinforcement learning AI model outputs, in response to the one or more training vectors, a treatment option recommendation for the respective user. The operations of 910 may be performed in accordance with examples as disclosed herein. In some examples, aspects of the operations of 910 may be performed by a model training component 650 as described with reference to FIG. 6.

At 915, the method may include applying a cost value or a reward value to the reinforcement learning AI model based on the corpus of data indicating a result of a treatment corresponding to the treatment option recommendation for the respective user. The operations of 915 may be performed in accordance with examples as disclosed herein. In some examples, aspects of the operations of 915 may be performed by a model training component 650 as described with reference to FIG. 6.

At 920, the method may include receiving, for a user, data indicating a diagnosis, a genomic profile, and a treatment history. The operations of 920 may be performed in accordance with examples as disclosed herein. In some examples, aspects of the operations of 920 may be performed by a data collection component 625 as described with reference to FIG. 6.

At 925, the method may include running a rules engine based on the genomic profile to determine one or more treatment modifications for the user. The operations of 925 may be performed in accordance with examples as disclosed herein. In some examples, aspects of the operations of 925 may be performed by a rules engine 630 as described with reference to FIG. 6.

At 930, the method may include inputting, to the trained reinforcement learning AI model, one or more vectors indicating the diagnosis, the genomic profile, and the treatment history, where the trained reinforcement learning AI model outputs, in response to the one or more vectors, a set of multiple treatment option recommendations and a set of multiple confidence metrics, where a respective confidence metric corresponds to a respective treatment option recommendation. The operations of 930 may be performed in accordance with examples as disclosed herein. In some examples, aspects of the operations of 930 may be performed by an AI model 635 as described with reference to FIG. 6.

At 935, the method may include outputting, to a user interface of a user device, the set of multiple treatment option recommendations and the set of multiple confidence metrics. The operations of 935 may be performed in accordance with examples as disclosed herein. In some examples, aspects of the operations of 935 may be performed by a treatment recommendation component 645 as described with reference to FIG. 6.

Figure 10:
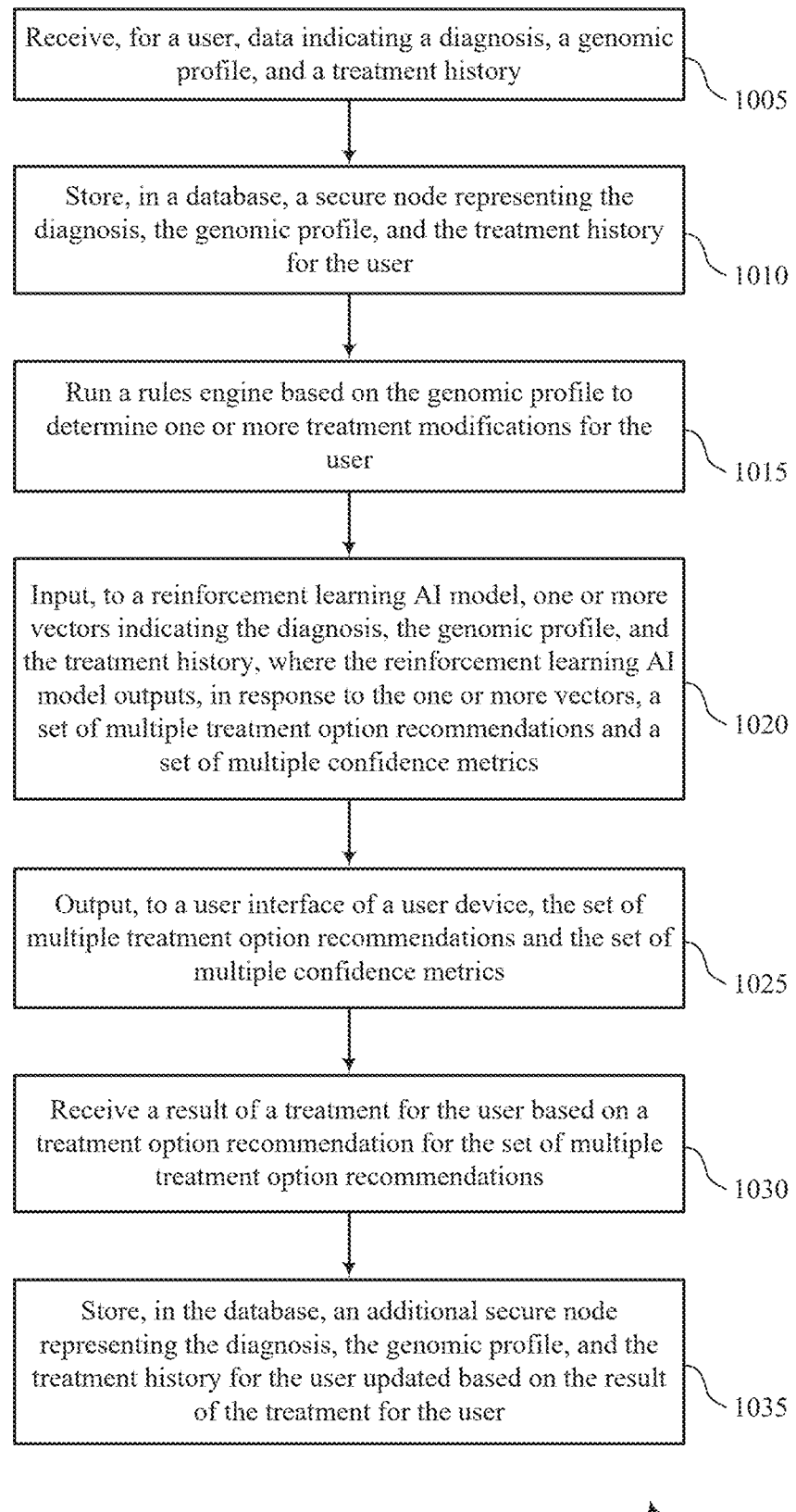

FIG. 10 shows a flowchart illustrating a method 1000 that supports treatment recommendations using genomic data and reinforcement learning in accordance with aspects of the present disclosure. The operations of the method 1000 may be implemented by a processing device or its components as described herein. For example, the operations of the method 1000 may be performed by a processing device or system, such as an application server, a database server, a cloud-based server or service, a worker server, a server cluster, a virtual machine, a container, a network device, a user device, or any combination of these or other computing devices. In some examples, a processing device or system may execute a set of instructions to control the functional elements of the processing device or system to perform the described functions. Additionally, or alternatively, the processing device or system may perform aspects of the described functions using special-purpose hardware.

At 1005, the method may include receiving, for a user, data indicating a diagnosis, a genomic profile, and a treatment history. The operations of 1005 may be performed in accordance with examples as disclosed herein. In some examples, aspects of the operations of 1005 may be performed by a data collection component 625 as described with reference to FIG. 6.

At 1010, the method may include storing, in a database, a secure node representing the diagnosis, the genomic profile, and the treatment history for the user. The operations of 1010 may be performed in accordance with examples as disclosed herein. In some examples, aspects of the operations of 1010 may be performed by a data storage component 655 as described with reference to FIG. 6.

At 1015, the method may include running a rules engine based on the genomic profile to determine one or more treatment modifications for the user. The operations of 1015 may be performed in accordance with examples as disclosed herein. In some examples, aspects of the operations of 1015 may be performed by a rules engine 630 as described with reference to FIG. 6.

At 1020, the method may include inputting, to a reinforcement learning AI model, one or more vectors indicating the diagnosis, the genomic profile, and the treatment history, where the reinforcement learning AI model outputs, in response to the one or more vectors, a set of multiple treatment option recommendations and a set of multiple confidence metrics, where a respective confidence metric corresponds to a respective treatment option recommendation. The operations of 1020 may be performed in accordance with examples as disclosed herein. In some examples, aspects of the operations of 1020 may be performed by an AI model 635 as described with reference to FIG. 6.

At 1025, the method may include outputting, to a user interface of a user device, the set of multiple treatment option recommendations and the set of multiple confidence metrics based on the at least one modified treatment option recommendation. The operations of 1025 may be performed in accordance with examples as disclosed herein. In some examples, aspects of the operations of 1025 may be performed by a treatment recommendation component 645 as described with reference to FIG. 6.

At 1030, the method may include receiving a result of a treatment for the user based on a treatment option recommendation for the set of multiple treatment option recommendations, where the treatment history for the user is updated based on the result of the treatment for the user. The operations of 1030 may be performed in accordance with examples as disclosed herein. In some examples, aspects of the operations of 1030 may be performed by a results collection component 670 as described with reference to FIG. 6.

At 1035, the method may include storing, in the database, an additional secure node representing the diagnosis, the genomic profile, and the treatment history for the user updated based on the result of the treatment for the user. The operations of 1035 may be performed in accordance with examples as disclosed herein. In some examples, aspects of the operations of 1035 may be performed by a data storage component 655 as described with reference to FIG. 6.

A method for recommending treatment options by an apparatus is described. The method may include receiving, for a user, data indicating a diagnosis, a genomic profile, and a treatment history, running a rules engine based on the genomic profile to determine one or more treatment modifications for the user, inputting, to a reinforcement learning AI model, one or more vectors indicating the diagnosis, the genomic profile, and the treatment history, where the reinforcement learning AI model outputs, in response to the one or more vectors, a set of multiple treatment option recommendations and a set of multiple confidence metrics, where a respective confidence metric corresponds to a respective treatment option recommendation, modifying at least one treatment option recommendation of the set of multiple treatment option recommendations based on the one or more treatment modifications for the user, and outputting, to a user interface of a user device, the set of multiple treatment option recommendations and the set of multiple confidence metrics based on the at least one modified treatment option recommendation.

An apparatus for recommending treatment options is described. The apparatus may include one or more memories storing processor executable code, and one or more processors coupled with the one or more memories. The one or more processors may individually or collectively be operable to execute the code to cause the apparatus to receive, for a user, data indicating a diagnosis, a genomic profile, and a treatment history, run a rules engine based on the genomic profile to determine one or more treatment modifications for the user, input, to a reinforcement learning AI model, one or more vectors indicating the diagnosis, the genomic profile, and the treatment history, where the reinforcement learning AI model outputs, in response to the one or more vectors, a set of multiple treatment option recommendations and a set of multiple confidence metrics, where a respective confidence metric corresponds to a respective treatment option recommendation, modify at least one treatment option recommendation of the set of multiple treatment option recommendations based on the one or more treatment modifications for the user, and output, to a user interface of a user device, the set of multiple treatment option recommendations and the set of multiple confidence metrics based on the at least one modified treatment option recommendation.

Another apparatus for recommending treatment options is described. The apparatus may include means for receiving, for a user, data indicating a diagnosis, a genomic profile, and a treatment history, means for running a rules engine based on the genomic profile to determine one or more treatment modifications for the user, means for inputting, to a reinforcement learning AI model, one or more vectors indicating the diagnosis, the genomic profile, and the treatment history, where the reinforcement learning AI model outputs, in response to the one or more vectors, a set of multiple treatment option recommendations and a set of multiple confidence metrics, where a respective confidence metric corresponds to a respective treatment option recommendation, means for modifying at least one treatment option recommendation of the set of multiple treatment option recommendations based on the one or more treatment modifications for the user, and means for outputting, to a user interface of a user device, the set of multiple treatment option recommendations and the set of multiple confidence metrics based on the at least one modified treatment option recommendation.

A non-transitory computer-readable medium storing code for recommending treatment options is described. The code may include instructions executable by one or more processors to receive, for a user, data indicating a diagnosis, a genomic profile, and a treatment history, run a rules engine based on the genomic profile to determine one or more treatment modifications for the user, input, to a reinforcement learning AI model, one or more vectors indicating the diagnosis, the genomic profile, and the treatment history, where the reinforcement learning AI model outputs, in response to the one or more vectors, a set of multiple treatment option recommendations and a set of multiple confidence metrics, where a respective confidence metric corresponds to a respective treatment option recommendation, modify at least one treatment option recommendation of the set of multiple treatment option recommendations based on the one or more treatment modifications for the user, and output, to a user interface of a user device, the set of multiple treatment option recommendations and the set of multiple confidence metrics based on the at least one modified treatment option recommendation.

Some examples of the method, apparatuses, and non-transitory computer-readable medium described herein may further include operations, features, means, or instructions for training the reinforcement learning AI model for the diagnosis based on a corpus of data for a set of multiple users, the corpus of data including a set of multiple respective genomic profiles, a set of multiple respective treatment histories, and a set of multiple respective results for the set of multiple users.

In some examples of the method, apparatuses, and non-transitory computer-readable medium described herein, training the reinforcement learning AI model may include operations, features, means, or instructions for inputting, to the reinforcement learning AI model, one or more training vectors indicating a set of training data from the corpus of data, the set of training data including a respective genomic profile and a respective treatment history for a respective user, where the reinforcement learning AI model outputs, in response to the one or more training vectors, a treatment option recommendation for the respective user and applying a cost value or a reward value to the reinforcement learning AI model based on the corpus of data indicating a result of a treatment corresponding to the treatment option recommendation for the respective user.

Some examples of the method, apparatuses, and non-transitory computer-readable medium described herein may further include operations, features, means, or instructions for receiving a result of a treatment for the user based on a treatment option recommendation for the set of multiple treatment option recommendations and retraining the reinforcement learning AI model for the diagnosis based on the result of the treatment for the user.

In some examples of the method, apparatuses, and non-transitory computer-readable medium described herein, the reinforcement learning AI model may be trained specific to the diagnosis and the method, apparatuses, and non-transitory computer-readable medium may include further operations, features, means, or instructions for training a second reinforcement learning AI model specific to a second diagnosis different from the diagnosis.

Some examples of the method, apparatuses, and non-transitory computer-readable medium described herein may further include operations, features, means, or instructions for storing, in a database, a secure node representing the diagnosis, the genomic profile, and the treatment history for the user.

Some examples of the method, apparatuses, and non-transitory computer-readable medium described herein may further include operations, features, means, or instructions for receiving a result of a treatment for the user based on a treatment option recommendation for the set of multiple treatment option recommendations, where the treatment history for the user may be updated based on the result of the treatment for the user and storing, in the database, an additional secure node representing the diagnosis, the genomic profile, and the treatment history for the user updated based on the result of the treatment for the user.

Some examples of the method, apparatuses, and non-transitory computer-readable medium described herein may further include operations, features, means, or instructions for generating a vector representing the user based on the diagnosis, the genomic profile, the treatment history, or a combination thereof and determining one or more other users similar to the user based on a vector similarity test for the vector representing the user and one or more other vectors representing the one or more other users in a vector space, where the set of multiple treatment option recommendations may be based on the one or more other users similar to the user.

In some examples of the method, apparatuses, and non-transitory computer-readable medium described herein, modifying the at least one treatment option recommendation may include operations, features, means, or instructions for removing a first treatment option recommendation from the set of multiple treatment option recommendations based on the one or more treatment modifications for the user, modifying a drug dosage recommendation for a second treatment option recommendation of the set of multiple treatment option recommendations based on the one or more treatment modifications for the user, removing a drug combination from a third treatment option recommendation of the set of multiple treatment option recommendations based on the one or more treatment modifications for the user, or any combination thereof.

In some examples of the method, apparatuses, and non-transitory computer-readable medium described herein, the one or more vectors input to the reinforcement learning AI model further indicate at least one treatment modification of the one or more treatment modifications for the user.

Some examples of the method, apparatuses, and non-transitory computer-readable medium described herein may further include operations, features, means, or instructions for receiving, via the user interface of the user device, a user input indicating an update to a treatment option recommendation of the set of multiple treatment option recommenda-
tions, inputting, to the reinforcement learning AI model, one
or more additional vectors indicating the diagnosis, the
genomic profile, the treatment history, and the update to the
treatment option recommendation, where the reinforcement
learning AI model outputs, in response to the one or more
additional vectors, an updated set of multiple treatment
option recommendations and an updated set of multiple
confidence metrics, where a respective updated confidence
metric corresponds to a respective updated treatment option
recommendation, and outputting, to the user interface of the
user device, the updated set of multiple treatment option
recommendations and the updated set of multiple confidence
metrics.

In some examples of the method, apparatuses, and non-
transitory computer-readable medium described herein, the
genomic profile includes a full genetic sequencing for the
user, a set of biomarkers for the user, or both.

In some examples of the method, apparatuses, and non-
transitory computer-readable medium described herein, the
reinforcement learning AI model includes a Double DQN.

Some examples of the method, apparatuses, and non-
transitory computer-readable medium described herein may
further include operations, features, means, or instructions
for outputting, to a system, a first treatment option recom-
mendation of the set of multiple treatment option recom-
mendations that corresponds to a first confidence metric
satisfying a confidence threshold.

Some examples of the method, apparatuses, and non-
transitory computer-readable medium described herein may
further include operations, features, means, or instructions
for refraining from outputting, to the system, the genomic
profile, the treatment history, or both for the user.

The following provides an overview of aspects of the
present disclosure:

Aspect 1: A method for recommending treatment options,
comprising: receiving, for a user, data indicating a diagnosis,
a genomic profile, and a treatment history; running a rules
engine based at least in part on the genomic profile to
determine one or more treatment modifications for the user;
inputting, to a reinforcement learning artificial intelligence
(AI) model, one or more vectors indicating the diagnosis, the
genomic profile, and the treatment history, wherein the
reinforcement learning AI model outputs, in response to the
one or more vectors, a plurality of treatment option recom-
mendations and a plurality of confidence metrics, wherein a
respective confidence metric corresponds to a respective
treatment option recommendation; modifying at least one
treatment option recommendation of the plurality of treat-
ment option recommendations based at least in part on the
one or more treatment modifications for the user; and
outputting, to a user interface of a user device, the plurality
of treatment option recommendations and the plurality of
confidence metrics based at least in part on the at least one
modified treatment option recommendation.

Aspect 2: The method of aspect 1, further comprising:
training the reinforcement learning AI model for the diag-
nosis based at least in part on a corpus of data for a plurality
of users, the corpus of data comprising a plurality of
respective genomic profiles, a plurality of respective treat-
ment histories, and a plurality of respective results for the
plurality of users.

Aspect 3: The method of aspect 2, wherein training the
reinforcement learning AI model comprises: inputting, to the
reinforcement learning AI model, one or more training
vectors indicating a set of training data from the corpus of
data, the set of training data comprising a respective genomic profile and a respective treatment history for a
respective user, wherein the reinforcement learning AI
model outputs, in response to the one or more training
vectors, a treatment option recommendation for the respec-
tive user; and applying a cost value or a reward value to the
reinforcement learning AI model based at least in part on the
corpus of data indicating a result of a treatment correspond-
ing to the treatment option recommendation for the respec-
tive user.

Aspect 4: The method of either of aspects 2 or 3, further
comprising: receiving a result of a treatment for the user
based at least in part on a treatment option recommendation
for the plurality of treatment option recommendations; and
retraining the reinforcement learning AI model for the
diagnosis based at least in part on the result of the treatment
for the user.

Aspect 5: The method of any of aspects 2 through 4,
wherein the reinforcement learning AI model is trained
specific to the diagnosis, the method further comprising:
training a second reinforcement learning AI model specific
to a second diagnosis different from the diagnosis.

Aspect 6: The method of any of aspects 1 through 5,
further comprising: storing, in a database, a secure node
representing the diagnosis, the genomic profile, and the
treatment history for the user.

Aspect 7: The method of aspect 6, further comprising:
receiving a result of a treatment for the user based at least in
part on a treatment option recommendation for the plurality
of treatment option recommendations, wherein the treatment
history for the user is updated based at least in part on the
result of the treatment for the user; and storing, in the
database, an additional secure node representing the diag-
nosis, the genomic profile, and the treatment history for the
user updated based at least in part on the result of the
treatment for the user.

Aspect 8: The method of any of aspects 1 through 7,
further comprising: generating a vector representing the user
based at least in part on the diagnosis, the genomic profile,
the treatment history, or a combination thereof; and deter-
mining one or more other users similar to the user based at
least in part on a vector similarity test for the vector
representing the user and one or more other vectors repre-
senting the one or more other users in a vector space,
wherein the plurality of treatment option recommendations
is based at least in part on the one or more other users similar
to the user.

Aspect 9: The method of any of aspects 1 through 8,
wherein modifying the at least one treatment option recom-
mendation comprises: removing a first treatment option
recommendation from the plurality of treatment option
recommendations based at least in part on the one or more
treatment modifications for the user; modifying a drug
dosage recommendation for a second treatment option rec-
ommendation of the plurality of treatment option recom-
mendations based at least in part on the one or more
treatment modifications for the user; removing a drug com-
bination from a third treatment option recommendation of
the plurality of treatment option recommendations based at
least in part on the one or more treatment modifications for
the user; or any combination thereof.

Aspect 10: The method of any of aspects 1 through 9,
wherein the one or more vectors input to the reinforcement
learning AI model further indicate at least one treatment
modification of the one or more treatment modifications for
the user.

Aspect 11: The method of any of aspects 1 through 10,
further comprising: receiving, via the user interface of the user device, a user input indicating an update to a treatment option recommendation of the plurality of treatment option recommendations; inputting, to the reinforcement learning AI model, one or more additional vectors indicating the diagnosis, the genomic profile, the treatment history, and the update to the treatment option recommendation, wherein the reinforcement learning AI model outputs, in response to the one or more additional vectors, an updated plurality of treatment option recommendations and an updated plurality of confidence metrics, wherein a respective updated confidence metric corresponds to a respective updated treatment option recommendation; and outputting, to the user interface of the user device, the updated plurality of treatment option recommendations and the updated plurality of confidence metrics.

Aspect 12: The method of any of aspects 1 through 11, wherein the genomic profile comprises a full genetic sequencing for the user, a set of biomarkers for the user, or both.

Aspect 13: The method of any of aspects 1 through 12, wherein the reinforcement learning AI model comprises a Double DQN.

Aspect 14: The method of any of aspects 1 through 13, further comprising: outputting, to a system, a first treatment option recommendation of the plurality of treatment option recommendations that corresponds to a first confidence metric satisfying a confidence threshold.

Aspect 15: The method of aspect 14, further comprising: refraining from outputting, to the system, the genomic profile, the treatment history, or both for the user.

Aspect 16: An apparatus for recommending treatment options, comprising one or more memories storing processor-executable code, and one or more processors coupled with the one or more memories and individually or collectively operable to execute the code to cause the apparatus to perform a method of any of aspects 1 through 15.

Aspect 17: An apparatus for recommending treatment options, comprising at least one means for performing a method of any of aspects 1 through 15.

Aspect 18: A non-transitory computer-readable medium storing code for recommending treatment options, the code comprising instructions executable by one or more processors to perform a method of any of aspects 1 through 15.

It should be noted that the methods described above describe possible implementations, and that the operations and the steps may be rearranged or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

As used herein, including in the claims, the article "a" before a noun is open-ended and understood to refer to "at least one" of those nouns or "one or more" of those nouns. Thus, the terms "a," "at least one," "one or more," "at least one of one or more" may be interchangeable. For example, if a claim recites "a component" that performs one or more functions, each of the individual functions may be performed by a single component or by any combination of multiple components. Thus, the term "a component" having characteristics or performing functions may refer to "at least one of one or more components" having a particular characteristic or performing a particular function. Subsequent reference to a component introduced with the article "a" using the terms "the" or "said" may refer to any or all of the one or more components. For example, a component introduced with the article "a" may be understood to mean "one or more components," and referring to "the component" subsequently in the claims may be understood to be equivalent to referring to "at least one of the one or more components." Similarly, subsequent reference to a component introduced as "one or more components" using the terms "the" or "said" may refer to any or all of the one or more components. For example, referring to "the one or more components" subsequently in the claims may be understood to be equivalent to referring to "at least one of the one or more components."

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein but is to be accorded the broadest scope consistent with the principles and novel features disclosed herein.

What is claimed is:

1. A method for recommending treatment options, comprising:

receiving, for a user, data indicating a diagnosis, a genomic profile, and a treatment history;

storing, at a database with encryption at rest, a set of data comprising at least a node or vector representation that indicates the diagnosis, the genomic profile, and the treatment history for the user, wherein the node or vector representation refrains from indicating personal identifiable information (PII) for the user;

running a rules-based engine based at least in part on the genomic profile to determine one or more treatment modifications for the user;

inputting, to a reinforcement learning artificial intelligence (AI) model trained based at least in part on one or more nodes or vector representations of the set of data, one or more vectors indicating the diagnosis, the genomic profile, and the treatment history, wherein the reinforcement learning AI model outputs, in response to the one or more vectors, a plurality of treatment option recommendations and a plurality of confidence metrics, wherein a respective confidence metric corresponds to a respective treatment option recommendation;

modifying at least one treatment option recommendation of the plurality of treatment option recommendations output by the reinforcement learning AI model based at least in part on the one or more treatment modifications for the user determined by the rules-based engine; and outputting, to a user interface of a user device, the plurality of treatment option recommendations and the plurality of confidence metrics based at least in part on the at least one modified treatment option recommendation.

2. The method of claim 1, further comprising:

training the reinforcement learning AI model for the diagnosis based at least in part on a corpus of data for a plurality of users, the corpus of data comprising a plurality of respective genomic profiles, a plurality of respective treatment histories, and a plurality of respective results for the plurality of users, wherein the corpus of data comprises the set of data.

3. The method of claim 2, wherein training the reinforcement learning AI model comprises:

inputting, to the reinforcement learning AI model, one or more training vectors indicating a set of training data from the corpus of data, the set of training data comprising a respective genomic profile and a respective treatment history for a respective user, wherein the reinforcement learning AI model outputs, in response to the one or more training vectors, a treatment option recommendation for the respective user; and applying a cost value or a reward value to the reinforcement learning AI model based at least in part on the corpus of data indicating a result of a treatment corresponding to the treatment option recommendation for the respective user.

4. The method of claim 2, further comprising:

receiving a result of a treatment for the user based at least in part on a treatment option recommendation for the plurality of treatment option recommendations; and retraining the reinforcement learning AI model for the diagnosis based at least in part on the result of the treatment for the user.

5. The method of claim 2, wherein the reinforcement learning AI model is trained specific to the diagnosis, the method further comprising:

training a second reinforcement learning AI model specific to a second diagnosis different from the diagnosis.

6. The method of claim 1, further comprising:

receiving a result of a treatment for the user based at least in part on a treatment option recommendation for the plurality of treatment option recommendations, wherein the treatment history for the user is updated based at least in part on the result of the treatment for the user; and storing, at the database, an additional secure node or vector representation representing the diagnosis, the genomic profile, and the treatment history for the user updated based at least in part on the result of the treatment for the user.

7. The method of claim 1, further comprising:
generating a vector representing the user based at least in part on the diagnosis, the genomic profile, the treatment history, or a combination thereof; and
determining one or more other users similar to the user based at least in part on a vector similarity test for the vector representing the user and one or more other vectors representing the one or more other users in a vector space, wherein the plurality of treatment option recommendations is based at least in part on the one or more other users similar to the user.

8. The method of claim 1, wherein modifying the at least one treatment option recommendation comprises:
removing a first treatment option recommendation from the plurality of treatment option recommendations based at least in part on the one or more treatment modifications for the user;
modifying a drug dosage recommendation for a second treatment option recommendation of the plurality of treatment option recommendations based at least in part on the one or more treatment modifications for the user;
removing a drug combination from a third treatment option recommendation of the plurality of treatment option recommendations based at least in part on the one or more treatment modifications for the user; or
any combination thereof.

9. The method of claim 1, wherein the one or more vectors input to the reinforcement learning AI model further indicate at least one treatment modification of the one or more treatment modifications for the user.

10. The method of claim 1, further comprising:
receiving, via the user interface of the user device, a user input indicating an update to a treatment option recommendation of the plurality of treatment option recommendations;
inputting, to the reinforcement learning AI model, one or more additional vectors indicating the diagnosis, the genomic profile, the treatment history, and the update to the treatment option recommendation, wherein the reinforcement learning AI model outputs, in response to the one or more additional vectors, an updated plurality of treatment option recommendations and an updated plurality of confidence metrics, wherein a respective updated confidence metric corresponds to a respective updated treatment option recommendation; and
outputting, to the user interface of the user device, the updated plurality of treatment option recommendations and the updated plurality of confidence metrics.

11. The method of claim 1, wherein the genomic profile comprises a full genetic sequencing for the user, a set of biomarkers for the user, or both.

12. The method of claim 1, wherein the reinforcement learning AI model comprises a Double Deep Q-Network (DQN).

13. The method of claim 1, further comprising:
outputting, to a system, a first treatment option recommendation of the plurality of treatment option recommendations that corresponds to a first confidence metric satisfying a confidence threshold.

14. The method of claim 13, further comprising:
refraining from outputting, to the system, the genomic profile, the treatment history, or both for the user.

15. An apparatus for recommending treatment options, comprising:
one or more memories storing processor-executable code; and one or more processors coupled with the one or more memories and individually or collectively operable to execute the code to cause the apparatus to:
receive, for a user, data indicating a diagnosis, a genomic profile, and a treatment history;
store, at a database with encryption at rest, a set of data comprising at least a node or vector representation that indicates the diagnosis, the genomic profile, and the treatment history for the user, wherein the node or vector representation refrains from indicating personal identifiable information (PII) for the user;
run a rules-based engine based at least in part on the genomic profile to determine one or more treatment modifications for the user;
input, to a reinforcement learning artificial intelligence (AI) model trained based at least in part on one or more nodes or vector representations of the set of data, one or more vectors indicating the diagnosis, the genomic profile, and the treatment history, wherein the reinforcement learning AI model outputs, in response to the one or more vectors, a plurality of treatment option recommendations and a plurality of confidence metrics, wherein a respective confidence metric corresponds to a respective treatment option recommendation;
modify at least one treatment option recommendation of the plurality of treatment option recommendations output by the reinforcement learning AI model based at least in part on the one or more treatment modifications for the user determined by the rules-based engine; and
output, to a user interface of a user device, the plurality of treatment option recommendations and the plurality of confidence metrics based at least in part on the at least one modified treatment option recommendation.

16. The apparatus of claim 15, wherein the one or more processors are individually or collectively further operable to execute the code to cause the apparatus to:
train the reinforcement learning AI model for the diagnosis based at least in part on a corpus of data for a plurality of users, the corpus of data comprising a plurality of respective genomic profiles, a plurality of respective treatment histories, and a plurality of respective results for the plurality of users, wherein the corpus of data comprises the set of data.

17. The apparatus of claim 15, wherein the one or more processors are individually or collectively further operable to execute the code to cause the apparatus to:
generate a vector representing the user based at least in part on the diagnosis, the genomic profile, the treatment history, or a combination thereof; and
determine one or more other users similar to the user based at least in part on a vector similarity test for the vector representing the user and one or more other vectors representing the one or more other users in a vector space, wherein the plurality of treatment option recommendations is based at least in part on the one or more other users similar to the user.

18. The apparatus of claim 15, wherein, to modify the at least one treatment option recommendation, the one or more processors are individually or collectively operable to execute the code to cause the apparatus to:
remove a first treatment option recommendation from the plurality of treatment option recommendations based at least in part on the one or more treatment modifications for the user;

modify a drug dosage recommendation for a second treatment option recommendation of the plurality of treatment option recommendations based at least in part on the one or more treatment modifications for the user;

remove a drug combination from a third treatment option recommendation of the plurality of treatment option recommendations based at least in part on the one or more treatment modifications for the user; or any combination thereof.

19. A non-transitory computer-readable medium storing code for recommending treatment options, the code comprising instructions executable by one or more processors to:

receive, for a user, data indicating a diagnosis, a genomic profile, and a treatment history;

store, at a database with encryption at rest, a set of data comprising at least a node or vector representation that indicates the diagnosis, the genomic profile, and the treatment history for the user, wherein the node or vector representation refrains from indicating personal identifiable information (PII) for the user;

run a rules-based engine based at least in part on the genomic profile to determine one or more treatment modifications for the user;

36 input, to a reinforcement learning artificial intelligence (AI) model trained based at least in part on one or more nodes or vector representations of the set of data, one or more vectors indicating the diagnosis, the genomic profile, and the treatment history, wherein the reinforcement learning AI model outputs, in response to the one or more vectors, a plurality of treatment option recommendations and a plurality of confidence metrics, wherein a respective confidence metric corresponds to a respective treatment option recommendation;

modify at least one treatment option recommendation of the plurality of treatment option recommendations output by the reinforcement learning AI model based at least in part on the one or more treatment modifications for the user determined by the rules-based engine; and output, to a user interface of a user device, the plurality of treatment option recommendations and the plurality of confidence metrics based at least in part on the at least one modified treatment option recommendation.

20. The method of claim 1, further comprising:

refraining from sharing the set of data with an external system.

* * * * *